United States Patent
Boock et al.

(10) Patent No.: US 10,045,723 B2
(45) Date of Patent: *Aug. 14, 2018

(54) ZWITTERION SURFACE MODIFICATIONS FOR CONTINUOUS SENSORS

(71) Applicant: DexCom, Inc., San Diego, CA (US)

(72) Inventors: Robert J. Boock, Carlsbad, CA (US); Chris W. Dring, Fremont, CA (US)

(73) Assignee: DexCom, Inc., San Diego, CA (US)

( * ) Notice: Subject to any disclaimer, the term of this patent is extended or adjusted under 35 U.S.C. 154(b) by 603 days.

This patent is subject to a terminal disclaimer.

(21) Appl. No.: 14/543,644

(22) Filed: Nov. 17, 2014

(65) Prior Publication Data
US 2015/0080691 A1    Mar. 19, 2015

Related U.S. Application Data

(63) Continuation of application No. 13/779,607, filed on Feb. 27, 2013.

(60) Provisional application No. 61/707,652, filed on Sep. 28, 2012.

(51) Int. Cl.
*A61B 5/1486* (2006.01)
*A61B 5/145* (2006.01)

(52) U.S. Cl.
CPC ........ *A61B 5/14865* (2013.01); *A61B 5/1486* (2013.01); *A61B 5/14532* (2013.01); *A61B 5/14546* (2013.01)

(58) Field of Classification Search
CPC ............ A61B 5/14532; A61B 5/14546; A61B 5/1486; A61B 5/14865
USPC ........................ 600/309, 345–366
See application file for complete search history.

(56) References Cited

U.S. PATENT DOCUMENTS

| | | | |
|---|---|---|---|
| 5,846,558 A | 12/1998 | Nielsen et al. |
| 5,976,529 A | 11/1999 | Navia et al. |
| 6,932,894 B2 | 8/2005 | Mao et al. |
| 7,670,470 B2 | 3/2010 | Mao et al. |
| 7,699,964 B2 | 4/2010 | Feldman et al. |
| 7,879,444 B2 | 2/2011 | Jiang et al. |

(Continued)

FOREIGN PATENT DOCUMENTS

| | | |
|---|---|---|
| JP | 2005-520172 A | 7/2005 |
| JP | 2009-540889 A | 11/2009 |

(Continued)

OTHER PUBLICATIONS

M. K. Khurana, et al. "Detection Mechanism of Metallized Carbon Epoxy Oxidase Enzyme Based Sensors", Electroanalysis, vol. 15, No. 12, 2003, p. 1023-1030.*

(Continued)

*Primary Examiner* — Navin Natnithithadha
(74) *Attorney, Agent, or Firm* — Knobbe Martens Olson & Bear LLP

(57) ABSTRACT

Devices are provided for measurement of an analyte concentration, e.g., glucose in a host. The device can include a sensor configured to generate a signal associated with a concentration of an analyte; and a sensing membrane located over the sensor. The sensing membrane comprises a diffusion resistance domain configured to control a flux of the analyte therethrough. The diffusion resistance domain comprises one or more zwitterionic compounds and a base polymer comprising both hydrophilic and hydrophobic regions.

24 Claims, 6 Drawing Sheets

(56) References Cited

U.S. PATENT DOCUMENTS

| | | |
|---|---|---|
| 8,103,456 B2 | 1/2012 | Doniger et al. |
| 8,147,666 B2 | 4/2012 | Mao et al. |
| 8,155,722 B2 | 4/2012 | Feldman et al. |
| 8,224,415 B2 | 7/2012 | Budiman |
| 8,255,030 B2 | 8/2012 | Petisce et al. |
| 8,574,660 B2 | 11/2013 | Weaver et al. |
| 8,632,838 B2 | 1/2014 | Roth et al. |
| 8,721,870 B2 * | 5/2014 | Oviatt, Jr. .......... A61B 5/14532 204/403.09 |
| 2003/0042137 A1 * | 3/2003 | Mao .................. A61B 5/14532 204/403.01 |
| 2005/0054909 A1 | 3/2005 | Petisce et al. |
| 2005/0090607 A1 | 4/2005 | Tapsak et al. |
| 2005/0095174 A1 | 5/2005 | Wolfe et al. |
| 2006/0004272 A1 | 1/2006 | Shah et al. |
| 2006/0257995 A1 | 11/2006 | Simpson et al. |
| 2006/0275860 A1 | 12/2006 | Kjaer et al. |
| 2007/0034512 A1 | 2/2007 | Yamaoka et al. |
| 2007/0197890 A1 | 8/2007 | Boock et al. |
| 2008/0034972 A1 | 2/2008 | Gough et al. |
| 2008/0214910 A1 | 9/2008 | Buck et al. |
| 2009/0099433 A1 | 4/2009 | Staib et al. |
| 2009/0247855 A1 | 10/2009 | Boock et al. |
| 2010/0041971 A1 | 2/2010 | Goode et al. |
| 2010/0168381 A1 | 7/2010 | O'Mahony et al. |
| 2010/0234793 A1 | 9/2010 | Dacey, Jr. et al. |
| 2010/0279377 A1 | 11/2010 | Shah et al. |
| 2011/0077490 A1 | 3/2011 | Simpson et al. |
| 2011/0180404 A1 | 7/2011 | Miyazaki et al. |
| 2011/0305872 A1 | 12/2011 | Li et al. |
| 2011/0305881 A1 | 12/2011 | Schultz et al. |
| 2011/0305895 A1 | 12/2011 | Roth et al. |
| 2011/0305898 A1 * | 12/2011 | Zhang .................. A61L 27/34 428/336 |
| 2011/0305909 A1 | 12/2011 | Weaver et al. |
| 2012/0197576 A1 | 8/2012 | Feldman et al. |
| 2012/0296186 A1 | 11/2012 | Ouyang et al. |
| 2013/0132416 A1 | 5/2013 | Hayter et al. |
| 2013/0178726 A1 | 7/2013 | Wang et al. |
| 2014/0024060 A1 | 1/2014 | Muller et al. |
| 2014/0094671 A1 | 4/2014 | Boock et al. |
| 2014/0094673 A1 | 4/2014 | Johnson et al. |
| 2014/0114156 A1 | 4/2014 | Bohm et al. |
| 2014/0275896 A1 | 9/2014 | Hughes et al. |
| 2014/0278189 A1 | 9/2014 | Vanslyke et al. |
| 2015/0080691 A1 | 3/2015 | Boock et al. |
| 2015/0289788 A1 | 10/2015 | Simpson et al. |
| 2017/0188902 A1 | 7/2017 | Wang et al. |
| 2017/0188905 A1 | 7/2017 | Lee et al. |
| 2017/0188921 A1 | 7/2017 | Wang et al. |
| 2017/0188922 A1 | 7/2017 | Lee et al. |

FOREIGN PATENT DOCUMENTS

| | | |
|---|---|---|
| WO | WO 2003-085372 | 10/2003 |
| WO | WO 2007-147475 | 12/2007 |
| WO | WO 2011-057219 | 5/2011 |
| WO | WO 2014-052080 | 4/2014 |

OTHER PUBLICATIONS

Chen et al. 2010. Polymer 51:5283-5293: Surface hydration: Principles and applications toward low-fouling/nonfouling biomaterials.

Jiang and Cao, 2010. Adv. Mater. 22:920-932. Ultralow-Fouling, Functionalizable, adn Hydrolyzable Zwitterionic Materials and Their Derivatives for Biological Applications.

Lin et al. Biosensors & Bloelectronics 47:451-460: Improving biocompatibility by surface modification techniques on implantable bloelectronics.

Yang et al. 2011. Biosensors & Bioelectronics 26(5):2454-2459: Zwitterionic poly(carboxybetaine) hydrogels for glucose biosensors in complex media.

U.S. Appl. No. 14/841,446, filed Aug. 31, 2015: US PTO Office Action dated Apr. 28, 2017.

ASTM Intl, Sep. 2012, Designation D3418-12 Standard Test Method for Transition Temperatures and enthalpies of Fusion and Crystallization of polymers by differential scanning c.

Chen et al., Polymer 51.5283-5293 (2010): Sufrace hydration: Principles and applications toward low-fouling/nonfouling biomaterials.

Yang et al., Biosensors & Bioelectronics 26(5):2454-2459 (2011): Zwitterionic poly(carboxybetaine) hydrogels for glucose biosensors in complex media.

U.S. Appl. No. 14/841,446, filed Aug. 31, 2015: USPTO Final Office Action dated Sep. 5, 2017.

U.S. Appl. No. 14/841,446, filed Aug. 31, 2015: USPTO OA dated Apr. 28, 2017.

U.S. Appl. No. 14/841,446, filed Aug. 31, 2015: USPTO Office Action dated Sep. 27, 2016.

\* cited by examiner

ZWITTERION SURFACE MODIFICATIONS FOR CONTINUOUS SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/779,607, filed Feb. 27, 2013, which claims the benefit of U.S. Provisional Application No. 61/707,652, filed Sep. 28, 2012. Each of the aforementioned applications is incorporated by reference herein in its entirety, and each is hereby expressly made a part of this specification.

FIELD OF THE INVENTION

Devices are provided for measurement of an analyte concentration, e.g., glucose in a host. The device can include a sensor configured to generate a signal associated with a concentration of an analyte; and a sensing membrane located over the sensor. The sensing membrane comprises a diffusion resistance domain configured to control a flux of the analyte therethrough. The diffusion resistance domain comprises one or more zwitterionic compounds and a base polymer comprising both hydrophilic and hydrophobic regions.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events. A variety of intravascular, transcutaneous and implantable sensors have been developed for continuously detecting and quantifying blood analytes, such as blood glucose levels.

However, one of the major performance issues for continuous glucose sensors is drift in the sensitivity of the sensor in-vivo. In sensors comprising polymer membranes with hydrophobic and hydrophilic components, drift can be caused by rearrangement of the hydrophobic and hydrophilic polymer components to either bring more hydrophilic components to the surface or otherwise rearrange to allow for increased access to hydrophilic components during hydration of the membrane system. Thus, in-vivo sensors with improved surface wetting are desired.

Additionally, in-vivo sensors may be coated for targeted drug/biologic delivery. The drug or biologic for delivery is typically coated on the surface of the sensor, and ideally releases in-vivo in a controlled and predictable way. Thus, in-vivo sensors with surface treatments which allow for controlled and predictable release of a drug or biologic for delivery to a subject's blood or tissue upon implantation are desired.

Finally, in-vivo sensors are susceptible to fouling from nonspecific protein adsorption and cell adhesion. Additionally, in-vivo sensors may trigger inflammatory responses, such as leukocyte activation, tissue fibrosis, etc., which may adversely impact sensor performance. Thus, in-vivo sensors with surface treatments which resist nonspecific protein adsorption and cell adhesion and/or reduce inflammatory response of the host are desired.

SUMMARY OF THE INVENTION

In a first aspect, a device is provided for measurement of an analyte concentration, the device comprising: a sensor configured to generate a signal associated with a concentration of an analyte and a sensing membrane located over the sensor. The sensing membrane comprises a bioprotective domain which interfaces with a biological fluid containing the analyte to be measured. In devices of this aspect, the bioprotective domain comprises a base polymer with both hydrophilic and hydrophobic regions and one or more zwitterionic compounds, precursors, or derivatives thereof.

In some embodiments, the bioprotective domain comprises up to about 0.1, 0.2, 0.3, 0.4, 0.5, 1, 2, or 5% wt zwitterionic compounds, precursors, or derivatives thereof.

In some embodiments, the zwitterionic compounds, precursors, or derivatives thereof comprise a betaine compound, precursor, or derivative thereof. In some embodiments, the zwitterionic compounds, precursors, or derivatives thereof comprise a carboxyl, sulfo, or phosphor betaine compound, precursor, or derivative thereof. In some embodiments, the zwitterionic compounds, precursors, or derivatives thereof comprise one or more selected from the group consisting of cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), poly(sulfobetaine) (pSB), and precursors or derivatives thereof. In some embodiments, the one or more the zwitterionic compounds or derivatives thereof comprise one or more selected from the group consisting of poly(carboxybetaine) (pCB), poly(sulfobetaine) (pSB), and precursors or derivatives thereof.

It will be appreciated that the above listing of zwitterionic compounds is by no means complete, and is not intended to be limiting. It is intended that other suitable zwitterionic compounds may be recognized by those of skill in the art. By way of further example, additional zwitterionic compounds, precursors, or derivatives thereof may include one or more selected from the group consisting of phosphorylcholine, phosphoryl ethanolamine, phosphatidyl ethanolamine, phosphoethanolamine, phosphatidyl serine, and precursors or derivatives thereof.

In some embodiments, the base polymer comprises at least one polymer selected from the group consisting of epoxies, polyolefins, polysiloxanes, polyethers, acrylics, polyesters, carbonates, and polyurethanes. In some related embodiments, the polyurethane comprises a polyurethane copolymer. In some embodiments, the base polymer comprises polyurethane.

In some embodiments, the sensor further comprises a diffusion resistance domain configured to control a flux of therethrough. In some embodiments, the bioprotective domain is part of a unitary bioprotective/diffusion resistance domain.

In some embodiments, the sensing membrane further comprises an enzyme domain comprising an enzyme selected from the group consisting of glucose oxidase, glucose dehydrogenase, galactose oxidase, cholesterol oxidase, amino acid oxidase, alcohol oxidase, lactate oxidase, and uricase. In some related embodiments, the enzyme is glucose oxidase.

In some embodiments, the sensor comprises an electrode.

In some embodiments, the device is configured for continuous measurement of an analyte concentration.

In some embodiments, the analyte is glucose.

In a second aspect, a device is provided for measurement of an analyte concentration, the device comprising: a sensor configured to generate a signal associated with a concentration of an analyte and a sensing membrane located over the sensor. The sensing membrane comprises a bioprotective domain configured to interface a biological fluid containing the analyte to be measured. In devices of this aspect, the bioprotective domain comprises a polyampholytic polymer with both hydrophilic and hydrophobic regions.

In some embodiments, the polyampholytic polymer comprises at least one polymer selected from the group consisting of epoxies, polyolefins, polysiloxanes, polyethers, acrylics, polyesters, carbonates, and polyurethanes. In some related embodiments, the polyurethane comprises a polyurethane copolymer. In some embodiments, the polyampholytic polymer comprises polyurethane.

In some embodiments, the polyampholytic polymer comprises up to about 0.1, 0.2, 0.3, 0.4, 0.5, 1, 2, or 5% wt monomers with charged end groups. In some embodiments, the numbers of cationic and anionic end groups in said polyampholytic polymer are about the same. In some embodiments, the number of cationic end groups is greater than the number of anionic end groups in said polyampholytic polymer. In some embodiments, the number of anionic end groups is greater than the number of cationic end groups in said polyampholytic polymer.

In some embodiments, the sensor further comprises a diffusion resistance domain configured to control a flux of therethrough. In some embodiments, the bioprotective domain is part of a unitary bioprotective/diffusion resistance domain.

In some embodiments, the sensing membrane further comprises an enzyme domain comprising an enzyme selected from the group consisting of glucose oxidase, glucose dehydrogenase, galactose oxidase, cholesterol oxidase, amino acid oxidase, alcohol oxidase, lactate oxidase, and uricase. In some related embodiments, the enzyme is glucose oxidase.

In some embodiments, the sensor comprises an electrode.

In some embodiments, the device is configured for continuous measurement of an analyte concentration.

In some embodiments, the analyte is glucose.

In a third aspect, a device is provided for measurement of an analyte concentration, the device comprising: a sensor configured to generate a signal associated with a concentration of an analyte, and a sensing membrane located over the sensor. In devices of this aspect, the surface of the sensing membrane most distal to the sensor is coated with a coating comprising one or more zwitterionic compounds, precursors, or derivatives thereof.

In some embodiments, the surface of the sensing membrane most distal to the sensor comprises surface-active end groups suitable for cross-linking with the zwitterionic compounds, precursors, or derivatives thereof; and wherein the zwitterionic compounds, precursors, or derivatives thereof are cross-linked to the surface-active end groups.

In some embodiments, the zwitterionic coating is not a hydrogel.

In some embodiments, the zwitterionic coating comprises up to about 0.1, 0.2, 0.3, 0.4, 0.5, 1, 2, 5, 10, 20, 30, 40, or 50% wt zwitterionic compounds, precursors, or derivatives thereof.

In some embodiments, the zwitterionic compounds, precursors, or derivatives thereof comprise a betaine compound, precursor, or derivative thereof. In some embodiments, the zwitterionic compounds, precursors, or derivatives thereof comprise a carboxyl, sulfo, or phosphor betaine compound, precursor, or derivative thereof. In some embodiments, the zwitterionic compounds, precursors, or derivatives thereof comprise one or more selected from the group consisting of cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), poly(sulfobetaine) (pSB), and precursors or derivatives thereof. In some embodiments, the one or more the zwitterionic compounds or derivatives thereof comprise one or more selected from the group consisting of poly(carboxybetaine) (pCB), poly(sulfobetaine) (pSB), and precursors or derivatives thereof.

In some embodiments where the zwitterionic compounds, precursors, or derivatives thereof comprise a betaine compound, precursor, or derivative thereof, the betaine compound, precursor, or derivative thereof is a hydrolyzable cationic betaine ester. In some related embodiments, the hydrolyzable cationic betaine ester is a cationic poly(carboxybetaine) (pCB) ester.

It will be appreciated that the above listing of zwitterionic compounds is by no means complete, and is not intended to be limiting. It is intended that other suitable zwitterionic compounds may be recognized by those of skill in the art. By way of further example, additional zwitterionic compounds, precursors, or derivatives thereof may include one or more selected from the group consisting of phosphorylcholine, phosphoryl ethanolamine, phosphatidyl ethanolamine, phosphoethanolamine, phosphatidyl serine, and precursors or derivatives thereof.

In some embodiments, the sensor membrane comprises a bioprotective domain located most distal to the sensor. In these embodiments, the bioprotective domain comprises at least one polymer selected from the group consisting of epoxies, polyolefins, polysiloxanes, polyethers, acrylics, polyesters, carbonates, and polyurethanes. In some related embodiments, the polyurethane comprises a polyurethane copolymer. In some embodiments, the base polymer comprises a polyurethane.

In some embodiments, the sensor membrane comprises a unitary bioprotective/diffusion resistance domain located most distal to the sensor. In these embodiments, the diffusion resistance domain comprises at least one polymer selected from the group consisting of epoxies, polyolefins, polysiloxanes, polyethers, acrylics, polyesters, carbonates, and polyurethanes. In some related embodiments, the polyurethane comprises a polyurethane copolymer. In some embodiments, the base polymer comprises a polyurethane.

In some embodiments, the sensing membrane further comprises an enzyme domain comprising an enzyme selected from the group consisting of glucose oxidase, glucose dehydrogenase, galactose oxidase, cholesterol oxidase, amino acid oxidase, alcohol oxidase, lactate oxidase, and uricase. In some related embodiments, the enzyme is glucose oxidase.

In some embodiments, the sensor comprises an electrode.

In some embodiments, the device is configured for continuous measurement of an analyte concentration.

In some embodiments, the analyte is glucose.

DETAILED DESCRIPTION

Figure 1:
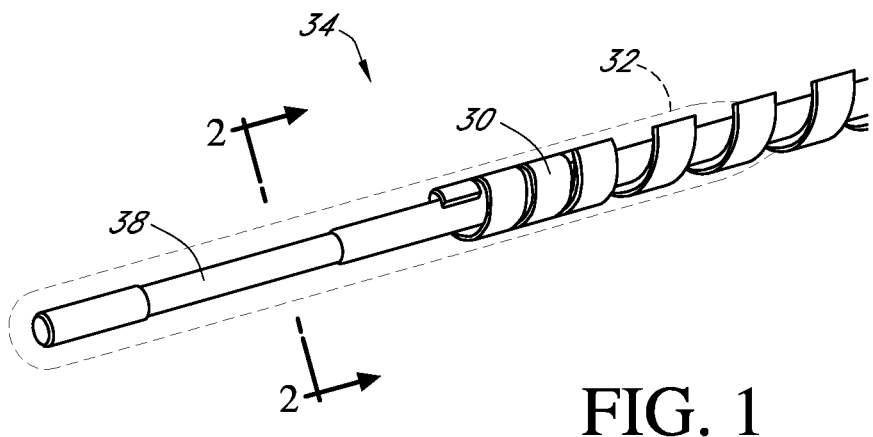
FIG. 1 is an expanded view of an exemplary embodiment of a continuous analyte sensor.

The following description and examples describe in detail some exemplary embodiments of devices and methods for providing measurement of an analyte concentration. It should be appreciated that there are numerous variations and modifications of the devices and methods described herein that are encompassed by the present invention. Accordingly, the description of a certain exemplary embodiment should not be deemed to limit the scope of the present invention.
Definitions In order to facilitate an understanding of the devices and methods described herein, a number of terms are defined below.

The term 'analyte' as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products. In some embodiments, the analyte for measurement by the sensing regions, devices, and methods is glucose. However, other analytes are contemplated as well, including, but not limited to: acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotimidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, Onchocerca volvulus, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to: insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The phrase 'continuous (or continual) analyte sensing' as used herein is a broad term, and is to be given its ordinary and customary meaning to a person of ordinary skill in the art (and is not to be limited to a special or customized meaning), and refers without limitation to the period in which monitoring of analyte concentration is continuously, continually, and or intermittently (but regularly) performed, for example, about every 5 to 10 minutes.

The terms 'operable connection,' 'operably connected,' and 'operably linked' as used herein are broad terms, and are to be given their ordinary and customary meaning to a person of ordinary skill in the art (and are not to be limited to a special or customized meaning), and refer without limitation to one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is 'operably linked' to the electronic circuitry.

The term 'host' as used herein is a broad term, and is to be given its ordinary and customary meaning to a person of ordinary skill in the art (and is not to be limited to a special or customized meaning), and refers without limitation to animals (e.g. humans) and plants.

The terms 'electrochemically reactive surface' and 'electroactive surface' as used herein are broad terms, and are to be given their ordinary and customary meaning to a person of ordinary skill in the art (and are not to be limited to a special or customized meaning), and refer without limitation to the surface of an electrode where an electrochemical reaction takes place. As one example, in a working electrode, $H_2O_2$ (hydrogen peroxide) produced by an enzyme-catalyzed reaction of an analyte being detected reacts and thereby creates a measurable electric current. For example, in the detection of glucose, glucose oxidase produces $H_2O_2$ as a byproduct. The $H_2O_2$ reacts with the surface of the working electrode to produce two protons ($2H^+$), two electrons ($2e^-$), and one molecule of oxygen ($O_2$), which produces the electric current being detected. In the case of the counter electrode, a reducible species, for example, $O_2$ is reduced at the electrode surface in order to balance the current being generated by the working electrode.

The terms 'sensing region,' 'sensor,' and 'sensing mechanism' as used herein are broad terms, and are to be given their ordinary and customary meaning to a person of ordinary skill in the art (and are not to be limited to a special or customized meaning), and refer without limitation to the region or mechanism of a monitoring device responsible for the detection of a particular analyte.

The terms 'raw data stream' and 'data stream' as used herein are broad terms, and are to be given their ordinary and customary meaning to a person of ordinary skill in the art (and are not to be limited to a special or customized meaning), and refer without limitation to an analog or digital signal directly related to the measured glucose concentration from the glucose sensor. In one example, the raw data stream is digital data in 'counts' converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term 'counts' as used herein is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term 'electrical potential' as used herein is a broad term, and is to be given its ordinary and customary meaning to a person of ordinary skill in the art (and is not to be limited to a special or customized meaning), and refers without limitation to the electrical potential difference between two points in a circuit which is the cause of the flow of a current.

The phrase 'distal to' as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a sensor include a membrane system having a bioprotective domain and an enzyme domain. If the sensor is deemed to be the point of reference and the bioprotective domain is positioned farther from the sensor than the enzyme domain, then the bioprotective domain is more distal to the sensor than the enzyme domain.

The phrase 'proximal to' as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a device include a membrane system having a bioprotective domain and an enzyme domain. If the sensor is deemed to be the point of reference and the enzyme domain is positioned nearer to the sensor than the bioprotective domain, then the enzyme domain is more proximal to the sensor than the bioprotective domain.

The terms 'interferents' and 'interfering species' as used herein are broad terms, and are to be given their ordinary and customary meaning to a person of ordinary skill in the art (and are not to be limited to a special or customized meaning), and refer without limitation to effects or species that interfere with the measurement of an analyte of interest in a sensor to produce a signal that does not accurately represent the analyte measurement. In an exemplary electrochemical sensor, interfering species can include compounds with an oxidation potential that overlaps with that of the analyte to be measured.

The term 'domain' as used herein is a broad term, and is to be given its ordinary and customary meaning to a person of ordinary skill in the art (and is not to be limited to a special or customized meaning), and refers without limitation to regions of a membrane that can be layers, uniform or non-uniform gradients (i.e., anisotropic) or provided as portions of the membrane.

The terms 'sensing membrane' and 'membrane system' as used herein are broad terms, and are to be given their ordinary and customary meaning to a person of ordinary skill in the art (and are not to be limited to a special or customized meaning), and refers without limitation to a permeable or semi-permeable membrane that can comprise one or more domains and constructed of materials of a few microns thickness or more, which are permeable to oxygen and may or may not be permeable to an analyte of interest. In one example, the sensing membrane or membrane system may comprise an immobilized glucose oxidase enzyme, which enables an electrochemical reaction to occur to measure a concentration of glucose.

The term 'baseline' as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation y=mx+b, the value of b represents the baseline of the signal.

The term 'sensitivity' as used herein is a broad term, and is to be given its ordinary and customary meaning to a person of ordinary skill in the art (and is not to be limited to a special or customized meaning), and refers without limitation to an amount of electrical current produced by a predetermined amount (unit) of the measured analyte. For example, in one embodiment, a sensor has a sensitivity (or slope) of from about 1 to about 100 picoAmps of current for every 1 mg/dL of glucose analyte.

The term 'dipole' or 'dipolar compound' as used herein is a broad term, and is to be given its ordinary and customary meaning to a person of ordinary skill in the art (and is not to be limited to a special or customized meaning), and refer without limitation to compounds in which a neutral molecule of the compound has a positive and negative electrical charge at different locations within the molecule. The positive and negative electrical charges within the molecule can be any non-zero charges up to and including full unit charges.

The terms 'zwitterion' and 'zwitterionic compound' as used herein are broad terms, and are to be given their ordinary and customary meaning to a person of ordinary skill in the art (and is not to be limited to a special or customized meaning), and refer without limitation to compounds in which a neutral molecule of the compound has a unit positive and unit negative electrical charge at different locations within the molecule. Such compounds are a type of dipolar compounds, and are also sometimes known as 'inner salts'.

A 'zwitterion precursor' or 'zwitterionic compound precursor' as used herein are broad terms, and are to be given their ordinary and customary meaning to a person of ordinary skill in the art (and is not to be limited to a special or customized meaning), and refer without limitation to any compound that is not itself a zwitterion, but may become a zwitterion in a final or transition state through chemical reaction. In some embodiments described herein, devices comprise zwitterion precursors that may be converted to zwitterions prior to in vivo implantation of the device. Alternatively, in some embodiments described herein, devices comprise zwitterion precursors that may be converted to zwitterions by some chemical reaction that occurs after in vivo implantation of the device.

A 'zwitterion derivative' or 'zwitterionic compound derivative' as used herein are broad terms, and are to be given their ordinary and customary meaning to a person of ordinary skill in the art (and is not to be limited to a special or customized meaning), and refer without limitation to any compound that is not itself a zwitterion, but rather is the product of a chemical reaction where a zwitterion is converted to a non-zwitterion. Such reactions may be reversible, such that under certain conditions zwitterion derivatives may act as zwitterion precursors. For example, hydrolyzable betaine esters formed from zwitterionic betaines are cationic zwitterion derivatives that under the appropriate conditions are capable of undergoing hydrolysis to revert to zwitterionic betaines.

The terms 'non-zwitterionic dipole' and 'non-zwitterionic dipolar compound' as used herein are broad terms, and are to be given their ordinary and customary meaning to a person of ordinary skill in the art (and is not to be limited to a special or customized meaning), and refer without limitation to compounds in which a neutral molecule of the compound have a positive and negative electrical charge at different locations within the molecule. The positive and negative electrical charges within the molecule can be any non-zero, but less than full unit, charges.

The term "polyampholytic polymer" as used herein is a broad term, and is to be given its ordinary and customary meaning to a person of ordinary skill in the art (and is not to be limited to a special or customized meaning), and refers without limitation to polymers comprising both cationic and anionic groups. Such polymers may be prepared to have about equal numbers of positive and negative charges, and thus the surface of such polymers may be about net neutrally charged. Alternatively, such polymers may be prepared to have an excess of either positive or negative charges, and thus the surface of such polymers may be net positively or negatively charged, respectively.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec (seconds); ° C. (degrees Centigrade).

Overview

Membrane systems of the preferred embodiments are suitable for use with implantable devices in contact with a biological fluid. For example, the membrane systems can be utilized with implantable devices, such as devices for monitoring and determining analyte levels in a biological fluid, for example, devices for monitoring glucose levels for individuals having diabetes. In some embodiments, the analyte-measuring device is a continuous device. The analyte-measuring device can employ any suitable sensing element to provide the raw signal, including but not limited to those involving enzymatic, chemical, physical, electrochemical, spectrophotometric, polarimetric, calorimetric, radiometric, immunochemical, or like elements.

Although some of the description that follows is directed at glucose-measuring devices, including the described membrane systems and methods for their use, these membrane systems are not limited to use in devices that measure or monitor glucose. These membrane systems are suitable for use in any of a variety of devices, including, for example, devices that detect and quantify other analytes present in biological fluids (e.g. cholesterol, amino acids, alcohol, galactose, and lactate), cell transplantation devices (see, for example, U.S. Pat. Nos. 6,015,572, 5,964,745,and 6,083,523), drug delivery devices (see, for example, U.S. Pat. Nos. 5,458,631, 5,820,589, and 5,972,369), and the like.

In one embodiment, the analyte sensor is an implantable glucose sensor, such as described with reference to U.S. Pat. No. 6,001,067 and U.S. Patent Publication No. US-2005-0027463-A1, which are incorporated herein by reference in their entirety. In another embodiment, the analyte sensor is a glucose sensor, such as described with reference to U.S. Patent Publication No. US-2006-0020187-A1, which is incorporated herein by reference in its entirety. In still other embodiments, the sensor is configured to be implanted in a host vessel or extra-corporeally, such as is described in U.S. Patent Publication No. US-2007-0027385-A1, U.S. Patent Publication No. US-2008-0119703-A1, U.S. Patent Publication No. US-2008-0108942-A1, and U.S. Patent Publication No. US-2007-0197890-A1, which are incorporated herein by reference in their entirety. In some embodiments, the sensor is configured as a dual-electrode sensor, such as described in U.S. Patent Publication No. US-2005-0143635-A1, U.S. Patent Publication No. US-2007-0027385-A1, U.S. Patent Publication No. US-2007-0213611-A1, and U.S. Patent Publication No. US-2008-0083617-A1, which are incorporated herein by reference in their entirety. In one alternative embodiment, the continuous glucose sensor comprises a sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In yet another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al. In some embodiments, the electrode system can be used with any of a variety of known in vivo analyte sensors or monitors, such as U.S. Pat. No. 7,157,528 to Ward; U.S. Pat. No. 6,212,416 to Ward et al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Publication No. EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. 5,985,129 to Gough et al.; PCT International Publication No. WO4/021877 to Caduff; U.S. Pat. No. 5,494,562 to Maley et al.; U.S. Pat. No. 6,120,676 to Heller et al.; and U.S. Pat. No. 6,542,765 to Guy et al. In general, it is understood that the disclosed embodiments are applicable to a variety of continuous analyte measuring device configurations.

In some embodiments, a long term sensor (e.g. wholly implantable or intravascular) is configured and arranged to function for a time period of from about 30 days or less to about one year or more (e.g. a sensor session). In some embodiments, a short term sensor (e.g. one that is transcutaneous or intravascular) is configured and arranged to function for a time period of from about a few hours to about 30 days, including a time period of about 1, 2, 3, 4, 5, 6, 7, 8, 9, 10, 11, 12, 13, 14, 15, 16, 17, 18, 19, 20, 21, 22, 23, 24, 25, 26, 27, 28 or 29 days (e.g., a sensor session). As used herein, the term 'sensor session' is a broad term and refers without limitation to the period of time the sensor is applied to (e.g. implanted in) the host or is being used to obtain sensor values. For example, in some embodiments, a sensor session extends from the time of sensor implantation (e.g. including insertion of the sensor into subcutaneous tissue and placing the sensor into fluid communication with a host's circulatory system) to the time when the sensor is removed.

Exemplary Glucose Sensor Configuration

FIG. 1 is an expanded view of an exemplary embodiment of a continuous analyte sensor 34, also referred to as an analyte sensor, illustrating the sensing mechanism. In some embodiments, the sensing mechanism is adapted for insertion under the host's skin, and the remaining body of the sensor (e.g. electronics, etc.) can reside ex vivo. In the illustrated embodiment, the analyte sensor 34 includes two electrodes, i.e., a working electrode 38 and at least one additional electrode 30, which may function as a counter or reference electrode, hereinafter referred to as the reference electrode 30.

It is contemplated that the electrode may be formed to have any of a variety of cross-sectional shapes. For example, in some embodiments, the electrode may be formed to have a circular or substantially circular shape, but in other embodiments, the electrode may be formed to have a cross-sectional shape that resembles an ellipse, a polygon (e.g. triangle, square, rectangle, parallelogram, trapezoid, pentagon, hexagon, octagon), or the like. In various embodiments, the cross-sectional shape of the electrode may be symmetrical, but in other embodiments, the cross-sectional shape may be asymmetrical. In some embodiments, each electrode may be formed from a fine wire with a diameter of from about 0.001 or less to about 0.050 inches or more, for example, and is formed from, e.g. a plated insulator, a plated wire, or bulk electrically conductive material. In some embodiments, the wire used to form a working electrode may be about 0.002, 0.003, 0.004, 0.005, 0.006, 0.007, 0.008, 0.009, 0.01, 0.015, 0.02, 0.025, 0.03, 0.035, 0.04 or 0.045 inches in diameter. In some embodiments, the working electrode may comprise a wire formed from a conductive material, such as platinum, platinum-black, platinum-iridium, palladium, graphite, gold, carbon, conductive polymer, alloys, or the like. Although the illustrated electrode configuration and associated text describe one method of forming a sensor, any of a variety of known sensor configurations can be employed with the analyte sensor system.

The working electrode 38 is configured to measure the concentration of an analyte, such as, but not limited to glucose, uric acid, cholesterol, lactate, and the like. In an enzymatic electrochemical sensor for detecting glucose, for example, the working electrode may measure the hydrogen peroxide produced by an enzyme catalyzed reaction of the analyte being detected and creates a measurable electric current. For example, in the detection of glucose wherein glucose oxidase (GOX) produces $H_2O_2$ as a byproduct, the $H_2O_2$ reacts with the surface of the working electrode producing two protons ($2H^+$), two electrons ($2e^-$) and one molecule of oxygen ($O_2$), which produces the electric current being detected.

An insulator may be provided to electrically insulate the working and reference electrodes. In this exemplary embodiment, the working electrode 38 is covered with an insulating material, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating because of its strength, lubricity, and electrical insulation properties. Generally, parylene is produced by vapor deposition and polymerization of para-xylylene (or its substituted derivatives). However, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as those marketed under the trade names AMC18, AMC148, AMC141, and AMC321 by Advanced Materials Components Express of Bellafonte, Pa. In some alternative embodiments, however, the working electrode may not require a coating of insulator.

In some embodiments, the reference electrode 30, which may function as a reference electrode alone, or as a dual reference and counter electrode, is formed from silver, silver/silver chloride, or the like. In some embodiments, the electrodes are juxtapositioned or twisted with or around each other, but it is contemplated, however, that other configurations are also possible. In one embodiment, the reference electrode 30 is helically wound around the working electrode 38. The assembly of wires may then be optionally coated together with an insulating material, similar to that described above, in order to provide an insulating attachment (e.g. securing together of the working and reference electrodes).

In embodiments wherein an outer insulator is disposed, a portion of the coated assembly structure can be stripped or otherwise removed, for example, by hand, excimer lasing, chemical etching, laser ablation, grit-blasting, or the like, to expose the electroactive surfaces. Alternatively, a portion of the electrode can be masked prior to depositing the insulator in order to maintain an exposed electroactive surface area.

In some embodiments, a radial window is formed through the insulating material to expose a circumferential electroactive surface of the working electrode. Additionally, sections of electroactive surface of the reference electrode are exposed. For example, the sections of electroactive surface can be masked during deposition of an outer insulating layer or etched after deposition of an outer insulating layer. In some applications, cellular attack or migration of cells to the sensor can cause reduced sensitivity or function of the device, particularly after the first day of implantation. However, when the exposed electroactive surface is distributed circumferentially about the sensor (e.g. as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

In some alternative embodiments, additional electrodes can be included within the assembly, for example, a three-electrode system (working, reference, and counter electrodes) and an additional working electrode (e.g. an electrode which can be used to generate oxygen, which is configured as a baseline subtracting electrode, or which is configured for measuring additional analytes). U.S. Pat. No. 7,081,195, U.S. Patent Publication No. US-2005-0143635-A1 and U.S. Patent Publication No. US-2007-0027385-A1, each of which are incorporated herein by reference, describe some systems and methods for implementing and using additional working, counter, and reference electrodes. In one implementation wherein the sensor comprises two working electrodes, the two working electrodes are juxtapositioned, around which the reference electrode is disposed (e.g. helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal comprising glucose and baseline signals, and the additional working electrode is configured to measure a baseline signal consisting of the baseline signal only. In these embodiments, the second working electrode may be configured to be substantially similar to the first working electrode, but without an enzyme disposed thereon. In this way, the baseline signal can be determined and subtracted from the first signal to generate a difference signal, i.e., a glucose-only signal that is substantially not subject to fluctuations in the baseline or interfering species on the signal, such as described in U.S. Patent Publication No. US-2005-0143635-A1, U.S. Patent Publication No. US-2007-0027385-A1, and U.S. Patent Publication No. US-2007-0213611-A1, and U.S. Patent Publication No. US-2008-0083617-A1, which are incorporated herein by reference in their entirety.

It has been found that in some electrode systems involving two working electrodes, i.e., in some dual-electrode systems, the working electrodes may sometimes be slightly different from each other. For instance, two working electrodes, even when manufactured from a single facility may slightly differ in thickness or permeability because of the electrodes' high sensitivity to environmental conditions (e.g. temperature, humidity) during fabrication. Accordingly, the working electrodes of a dual-electrode system may sometimes have varying diffusion, membrane thickness, and diffusion characteristics. As a result, the above-described difference signal (i.e., a glucose-only signal, generated from subtracting the baseline signal from the first signal) may not be completely accurate. To mitigate this, it is contemplated that in some dual-electrode systems, both working electrodes may be fabricated with one or more membranes that each includes a bioprotective layer, which is described in more detail elsewhere herein.

It is contemplated that the sensing region may include any of a variety of electrode configurations. For example, in some embodiments, in addition to one or more glucose-measuring working electrodes, the sensing region may also include a reference electrode or other electrodes associated with the working electrode. In these particular embodiments, the sensing region may also include a separate reference or counter electrode associated with one or more optional auxiliary working electrodes. In other embodiments, the sensing region may include a glucose-measuring working electrode, an auxiliary working electrode, two counter electrodes (one for each working electrode), and one shared reference electrode. In yet other embodiments, the sensing region may include a glucose-measuring working electrode, an auxiliary working electrode, two reference electrodes, and one shared counter electrode.

U.S. Patent Publication No. US-2011-002712-A1, U.S. Patent Publication No. US-2008-0119703-A1 and U.S. Patent Publication No. US-2005-0245799-A1, each of which is incorporated herein by reference in its entirety, describe additional configurations for using the continuous sensor in different body locations. In some embodiments, the sensor is configured for transcutaneous implantation in the host. In alternative embodiments, the sensor is configured for insertion into the circulatory system, such as a peripheral vein or artery. However, in other embodiments, the sensor is configured for insertion into the central circulatory system, such as but not limited to the vena cava. In still other embodiments, the sensor can be placed in an extracorporeal circulation system, such as but not limited to an intravascular access device providing extracorporeal access to a blood vessel, an intravenous fluid infusion system, an extracorporeal blood chemistry analysis device, a dialysis machine, a heart-lung machine (i.e., a device used to provide blood circulation and oxygenation while the heart is stopped during heart surgery), etc. In still other embodiments, the sensor can be configured to be wholly implantable, as described in U.S. Pat. No. 6,001,067.

Figure 4A:
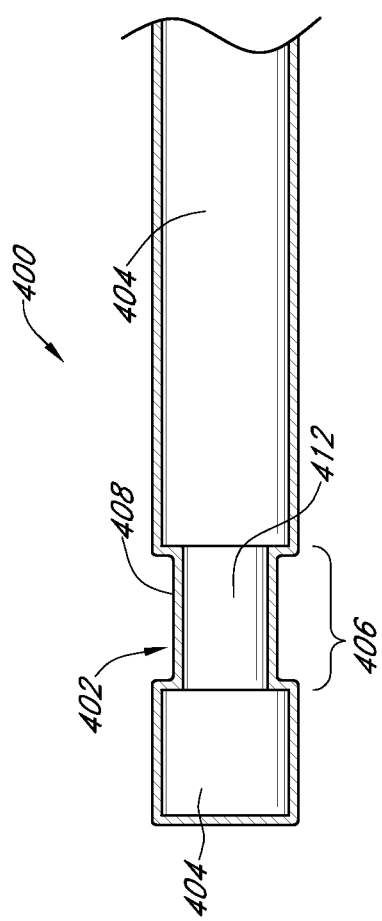
FIG. 4A is a side view schematic illustrating an in vivo portion of a continuous analyte sensor, in one embodiment.
Figure 4C:
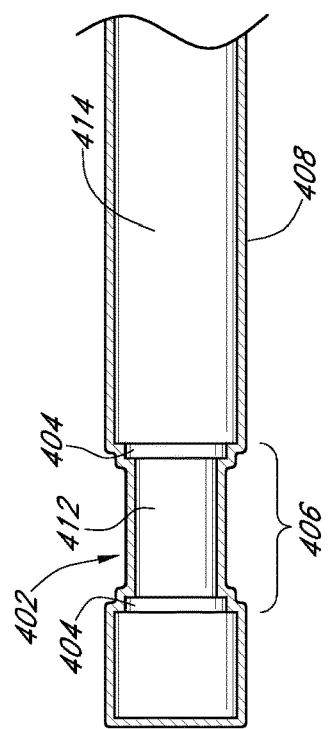
FIG. 4C is a side view schematic illustrating an in vivo portion of a continuous analyte sensor, in one embodiment.
Figure 4B:
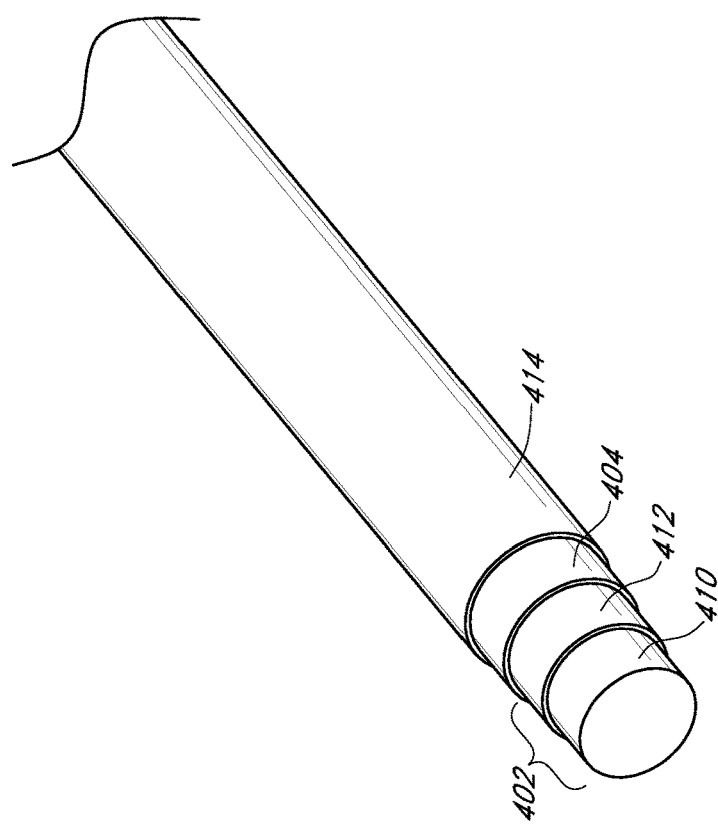
FIG. 4B is a perspective view schematic illustrating an in vivo portion of a continuous analyte sensor, in one embodiment.

FIGS. 4A through 4C illustrate an alternate embodiment of the in vivo portion of a continuous analyte sensor 400, which includes an elongated conductive body 402. The elongated conductive body 402 includes a core 410 (see FIG. 4B) and a first layer 412 at least partially surrounding the core. The first layer includes a working electrode (for example, located in window 406) and a membrane 408 located over the working electrode. In some embodiments, the core and first layer can be of a single material (such as, for example, platinum). In some embodiments, the elongated conductive body is a composite of at least two materials, such as a composite of two conductive materials, or a composite of at least one conductive material and at least one non-conductive material. In some embodiments, the elongated conductive body comprises a plurality of layers. In certain embodiments, there are at least two concentric or annular layers, such as a core formed of a first material and a first layer formed of a second material. However, additional layers can be included in some embodiments. In some embodiments, the layers are coaxial.

The elongated conductive body may be long and thin, yet flexible and strong. For example, in some embodiments, the smallest dimension of the elongated conductive body is less than about 0.1 inches, 0.075 inches, 0.05 inches, 0.025 inches, 0.01 inches, 0.004 inches, or 0.002 inches. While the elongated conductive body is illustrated in FIGS. 4A through 4C as having a circular cross-section, in other embodiments the cross-section of the elongated conductive body can be ovoid, rectangular, triangular, polyhedral, star-shaped, C-shaped, T-shaped, X-shaped, Y-Shaped, irregular, or the like. In one embodiment, a conductive wire electrode is employed as a core. To such a clad electrode, two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

The materials used to form the elongated conductive body (such as, for example, stainless steel, titanium, tantalum, platinum, platinum-iridium, iridium, certain polymers, and/or the like) can be strong and hard, and therefore are resistant to breakage. In some embodiments, the sensor's small diameter provides flexibility to these materials, and therefore to the sensor as a whole. Thus, the sensor can withstand repeated forces applied to it by surrounding tissue.

In addition to providing structural support, resiliency and flexibility, in some embodiments, the core 410, or a component thereof, provides electrical conduction for an electrical signal from the working electrode to sensor electronics (not shown). In some embodiments, the core 410 comprises a conductive material, such as stainless steel, titanium, tantalum, a conductive polymer, and/or the like. However, in other embodiments, the core is formed from a non-conductive material, such as a non-conductive polymer. In yet other embodiments, the core comprises a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is a conductive material selected to provide electrical conduction between the core and the first layer, and/or to attach the first layer to the core (that is, if the first layer is formed of a material that does not attach well to the core material). In another embodiment, the core is formed of a non-conductive material (such as, for example, a non-conductive metal and/or a non-conductive polymer) and the first layer is formed of a conductive material, such as stainless steel, titanium, tantalum, a conductive polymer, and/or the like. The core and the first layer can be of a single (or same) material, such as platinum. One skilled in the art appreciates that additional configurations are possible.

Referring again to FIGS. 4A-4C, the first layer 412 can be formed of a conductive material and the working electrode can be an exposed portion of the surface of the first layer 412. Accordingly, the first layer 412 can be formed of a material configured to provide a suitable electroactive surface for the working electrode, a material such as, but not limited to, platinum, platinum-iridium, gold, palladium, iridium, graphite, carbon, a conductive polymer, an alloy and/or the like.

As illustrated in FIG. 4B-4C, a second layer 404 surrounds at least a portion of the first layer 412, thereby defining the boundaries of the working electrode. In some embodiments, the second layer 404 serves as an insulator and is formed of an insulating material, such as polyimide, polyurethane, parylene, or any other known insulating materials. For example, in one embodiment the second layer is disposed on the first layer and configured such that the working electrode is exposed via window 406. In some embodiments, an elongated conductive body, including the core, the first layer and the second layer, is provided. A portion of the second layer can be removed to form a window 406, through which the electroactive surface of the working electrode (that is, the exposed surface of the first layer 412) is exposed. In some embodiments, a portion of the second and (optionally) third layers can be removed to form the window 406, thus exposing the working electrode. Removal of coating materials from one or more layers of the elongated conductive body (for example, to expose the electroactive surface of the working electrode) can be performed by hand, excimer lasing, chemical etching, laser ablation, grit-blasting, or the like.

The sensor can further comprise a third layer 414 comprising a conductive material. For example, the third layer 414 may comprise a reference electrode, which may be formed of a silver-containing material that is applied onto the second layer 404 (that is, the insulator).

The elongated conductive body 402 can further comprise one or more intermediate layers (not shown) located between the core 410 and the first layer 412. For example, the intermediate layer can be one or more of an insulator, a conductor, a polymer, and/or an adhesive.

It is contemplated that the ratio between the thickness of the silver/silver chloride layer and the thickness of an insulator (such as, for example, polyurethane or polyimide) layer can be controlled, so as to allow for a certain error margin (that is, an error margin associated with the etching process) that would not result in a defective sensor (for example, due to a defect resulting from an etching process that cuts into a depth more than intended, thereby unintentionally exposing an electroactive surface). This ratio may be different depending on the type of etching process used, whether it is laser ablation, grit blasting, chemical etching, or some other etching method. In one embodiment in which laser ablation is performed to remove a silver/silver chloride layer and a polyurethane layer, the ratio of the thickness of the silver/silver chloride layer and the thickness of the polyurethane layer can be from about 1:5 to about 1:1, or from about 1:3 to about 1:2.

In some embodiments, the core 410 comprises a non-conductive polymer and the first layer 412 comprises a conductive material. Such a sensor configuration can advantageously provide reduced material costs, in that it replaces a typically expensive material with an inexpensive material. For example, the core 410 can be formed of a non-conductive polymer, such as, a nylon or polyester filament, string or cord, which can be coated and/or plated with a conductive material, such as platinum, platinum-iridium, gold, palladium, iridium, graphite, carbon, a conductive polymer, and allows or combinations thereof.

Figure 2A:
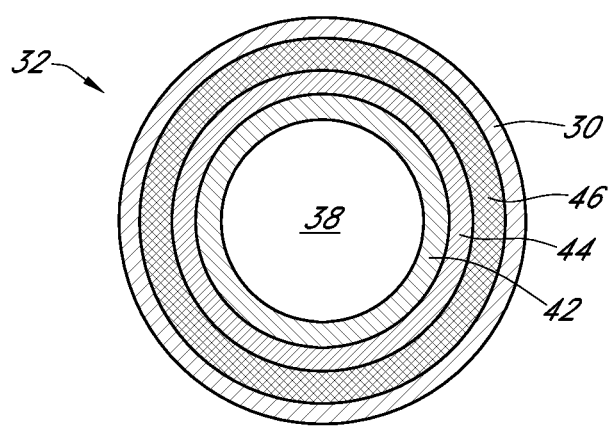
FIGS. 2A-2C are cross-sectional views through the sensor of FIG. 1 on line 2-2, illustrating various embodiments of the membrane system.
Figure 2B:
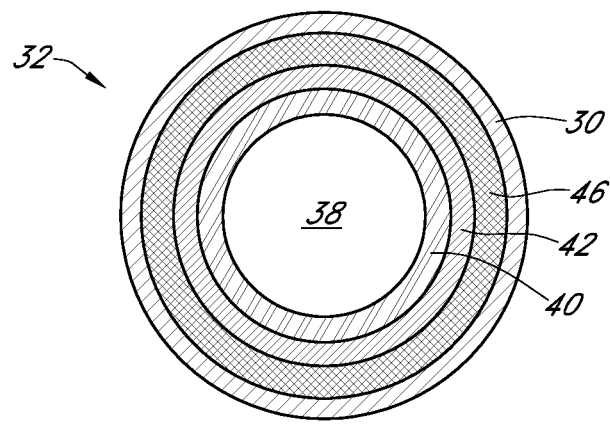
Figure 2C:
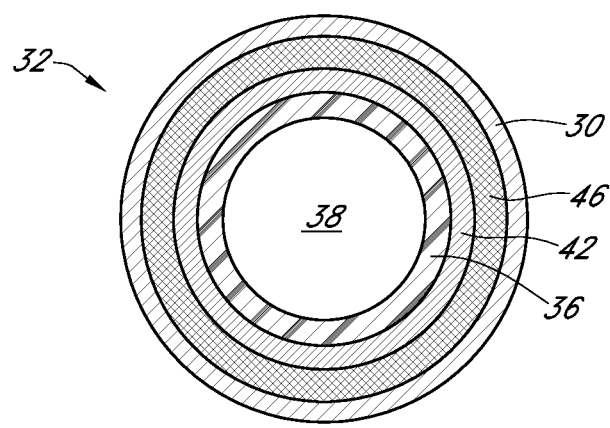
Figure 4D:
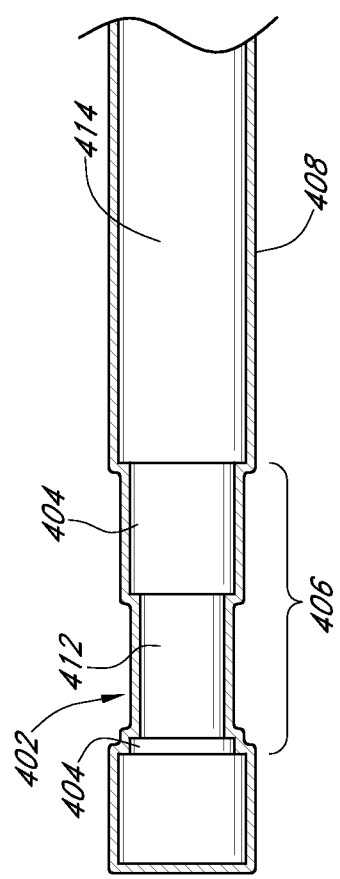
FIG. 4D is a cross-sectional/side-view schematic illustrating an in vivo portion of a continuous analyte sensor, in one embodiment.

As illustrated in FIGS. 4C and 4D, the sensor can also include a membrane 408, such as those discussed elsewhere herein, for example, with reference to FIGS. 2A-2C. The membrane 408 can include an enzyme layer (not shown), as described elsewhere herein. For example, the enzyme layer can include a catalyst or enzyme configured to react with an analyte. For example, the enzyme layer can be an immobilized enzyme layer including glucose oxidase. In other embodiments, the enzyme layer can be impregnated with other oxidases, including, for example, galactose oxidase, cholesterol oxidase, amino acid oxidase, alcohol oxidase, lactate oxidase, or uricase.

FIG. 4B is a schematic illustrating an embodiment of an elongated conductive body 402, or elongated body, wherein the elongated conductive body is formed from at least two materials and/or layers of conductive material, as described in greater detail elsewhere herein. The term "electrode" can be used herein to refer to the elongated conductive body, which includes the electroactive surface that detects the analyte. In some embodiments, the elongated conductive body provides an electrical connection between the electroactive surface (that is, the working electrode) and the sensor electronics (not shown). In certain embodiments, each electrode (that is, the elongated conductive body on which the electroactive surface is located) is formed from a fine wire with a diameter of from about 0.001 inches or less to about 0.01 inches or more. Each electrode can be formed from, for example, a plated insulator, a plated wire, or bulk electrically conductive material. For example, in some embodiments, the wire and/or elongated conductive body used to form a working electrode is about 0.002, 0.003, 0.004, 0.005, 0.006, 0.007, 0.008, 0.009, 0.01, 0.015, 0.02, 0.025, 0.03, 0.035, 0.04 or 0.045 inches in diameter.

Furthermore, the first layer can comprise an electroactive surface (that is, the portion exposed through the window 406). The exposed electroactive surface can be the working electrode. For example, if the sensor is an enzymatic electrochemical analyte sensor, the analyte enzymatically reacts with an enzyme in the membrane covering at least a portion of the electroactive surface. The reaction can generate electrons ($e^-$) that are detected at the electroactive surface as a measurable electronic current. For example, in the detection of glucose wherein glucose oxidase produces hydrogen peroxide as a byproduct, hydrogen peroxide reacts with the surface of the working electrode producing two protons ($2H^+$), two electrons ($2e^-$) and one molecule of oxygen ($O_2$), which produces the electronic current being detected.

As previously described with reference to FIG. 4A and as illustrated in FIG. 4C, an insulator 404 is disposed on at least a portion of the elongated conductive body 402. In some embodiments, the sensor is configured and arranged such that the elongated body includes a core 410 and a first layer 412, and a portion of the first layer 412 is exposed via window 406 in the insulator 404. In other embodiments, the sensor is configured and arranged such that the elongated body 402 includes a core 410 embedded in an insulator 404, and a portion of the core 410 is exposed via the window 406 in the insulator 404. For example, the insulating material can be applied to the elongated body 402 (by, for example, screen-, ink-jet and/or block-print) in a configuration designed to leave at least a portion of the first layer's 412 surface (or the core's 410 surface) exposed. For example, the insulating material can be printed in a pattern that does not cover a portion of the elongated body 402. Alternatively, a portion of the elongated body 402 can be masked prior to application of the insulating material. Removal of the mask, after insulating material application, can expose the portion of the elongated body 402.

In some embodiments, the insulating material 404 comprises a polymer, for example, a non-conductive (that is, dielectric) polymer. Dip-coating, spray-coating, vapor-deposition, printing and/or other thin film and/or thick film coating or deposition techniques can be used to deposit the insulating material on the elongated body 402 and/or core 410. For example, in some embodiments, the insulating material is applied as a layer of from about less than 5 microns, or from 5, 10 or 15-microns to about 20, 25, 30 or 35-microns or more in thickness. The insulator can be applied as a single layer of material, or as two or more layers, which are comprised of either the same or different materials, as described elsewhere herein. Alternatively, the conductive core may not require a coating of insulator. In some embodiments, the insulating material defines an electroactive surface of the analyte sensor (that is, the working electrode). For example, a surface of the conductive core (such as, for example, a portion of the first layer 412) can either remain exposed during the insulator application, or a portion of applied insulator can be removed to expose a portion of the conductive core's surface, as described above.

In some embodiments, in which the sensor has an insulated elongated body or an insulator disposed upon a conductive structure, a portion of the insulating material can be stripped or otherwise removed, for example, by hand, excimer lasing, chemical etching, laser ablation, grit-blasting (such as, for example, with sodium bicarbonate or other suitable grit), or the like, to expose the electroactive surfaces. In one exemplary embodiment, grit blasting is implemented to expose the electroactive surface(s), for example, by utilizing a grit material that is sufficiently hard to ablate the polymer material yet also sufficiently soft so as to minimize or avoid damage to the underlying metal electrode (for example, a platinum electrode). Although a variety of "grit" materials can be used (such as, for example, sand, talc, walnut shell, ground plastic, sea salt, and the like), in some embodiments, sodium bicarbonate is an advantageous grit-material because it is sufficiently hard to ablate, e.g., a parylene coating without damaging, e.g., an underlying platinum conductor. An additional advantage of sodium bicarbonate blasting includes its polishing action on the metal as it strips the polymer layer, thereby eliminating a cleaning step that might otherwise be necessary. Alternatively, a portion of an electrode or other conductive body can be masked prior to depositing the insulator in order to maintain an exposed electroactive surface area.

The electroactive surface of the working electrode can be exposed by formation of a window 406 in the insulator 404. The electroactive window 406 of the working electrode can be configured to measure the concentration of an analyte.

In some embodiments, a silver wire is formed onto and/or fabricated into the sensor and subsequently chloridized to form a silver/silver chloride reference electrode. Advantageously, chloridizing the silver wire as described herein enables the manufacture of a reference electrode with good in vivo performance. By controlling the quantity and amount of chloridization of the silver to form silver/silver chloride, improved break-in time, stability of the reference electrode and extended life can be obtained in some embodiments. Additionally, use of silver chloride as described above allows for relatively inexpensive and simple manufacture of the reference electrode.

Referring to FIGS. 4B-4C, the reference electrode 414 can comprise a silver-containing material (e.g., silver/silver chloride) applied over at least a portion of the insulating material 404, as discussed in greater detail elsewhere herein. For example, the silver-containing material can be applied using thin film and/or thick film techniques, such as but not limited to dipping, spraying, printing, electro-depositing, vapor deposition, spin coating, and sputter deposition, as described elsewhere herein. For example, a silver or silver chloride-containing paint (or similar formulation) can be applied to a reel of the insulated conductive core. Alternatively, the reel of insulated elongated body (or core) is cut into single unit pieces (that is, "singularized"), and silver-containing ink is pad printed thereon. In still other embodiments, the silver-containing material is applied as a silver foil. For example, an adhesive can be applied to an insulated elongated body, around which the silver foil can then be wrapped in. Alternatively, the sensor can be rolled in Ag/AgCl particles, such that a sufficient amount of silver sticks to and/or embeds into and/or otherwise adheres to the adhesive for the particles to function as the reference electrode. In some embodiments, the sensor's reference electrode includes a sufficient amount of chloridized silver that the sensor measures and/or detects the analyte for at least three days.

FIG. 2A is a cross-sectional view through the sensor of FIG. 1 on line 2-2, illustrating one embodiment of the membrane system 32. In this particular embodiment, the membrane system includes an enzyme domain 42, a diffusion resistance domain 44, and a bioprotective domain 46 located around the working electrode 38, all of which are described in more detail elsewhere herein. In some embodiments, a unitary diffusion resistance domain and bioprotective domain may be included in the membrane system (e.g., wherein the functionality of both domains is incorporated into one domain, i.e., the bioprotective domain). In some embodiments, the sensor is configured for short-term implantation (e.g., from about 1 to 30 days). However, it is understood that the membrane system 32 can be modified for use in other devices, for example, by including only one or more of the domains, or additional domains.

In some embodiments, the membrane system may include a bioprotective domain 46, also referred to as a cell-impermeable domain or biointerface domain, comprising a surface-modified base polymer as described in more detail elsewhere herein. However, the sensing membranes 32 of some embodiments can also include a plurality of domains or layers including, for example, an electrode domain (e.g., as illustrated in the FIG. 2C), an interference domain (e.g., as illustrated in FIG. 2B), or a cell disruptive domain (not shown), such as described in more detail elsewhere herein and in U.S. Patent Publication No. US-2006-0036145-A1, which is incorporated herein by reference in its entirety.

It is to be understood that sensing membranes modified for other sensors, for example, may include fewer or additional layers. For example, in some embodiments, the membrane system may comprise one electrode layer, one enzyme layer, and two bioprotective layers, but in other embodiments, the membrane system may comprise one electrode layer, two enzyme layers, and one bioprotective layer. In some embodiments, the bioprotective layer may be configured to function as the diffusion resistance domain and control the flux of the analyte (e.g., glucose) to the underlying membrane layers.

In some embodiments, one or more domains of the sensing membranes may be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some embodiments, the sensing membrane can be deposited on the electroactive surfaces of the electrode material using known thin or thick film techniques (for example, spraying, electro-depositing, dipping, or the like). It should be appreciated that the sensing membrane located over the working electrode does not have to have the same structure as the sensing membrane located over the reference electrode; for example, the enzyme domain deposited over the working electrode does not necessarily need to be deposited over the reference or counter electrodes.

Although the exemplary embodiments illustrated in FIGS. 2A-2C involve circumferentially extending membrane systems, the membranes described herein may be applied to any planar or non-planar surface, for example, the substrate-based sensor structure of U.S. Pat. No. 6,565,509 to Say et al.

Sensor Electronics

In general, analyte sensor systems have electronics associated therewith, also referred to as a 'computer system' that can include hardware, firmware, or software that enable measurement and processing of data associated with analyte levels in the host. In one exemplary embodiment of an electrochemical sensor, the electronics include a potentiostat, a power source for providing power to the sensor, and other components useful for signal processing. In additional embodiments, some or all of the electronics can be in wired or wireless communication with the sensor or other portions of the electronics. For example, a potentiostat disposed on the device can be wired to the remaining electronics (e.g. a processor, a recorder, a transmitter, a receiver, etc.), which reside on the bedside. In another example, some portion of the electronics is wirelessly connected to another portion of the electronics (e.g., a receiver), such as by infrared (IR) or RF. It is contemplated that other embodiments of electronics may be useful for providing sensor data output, such as those described in U.S. Patent Publication No. US-2005-0192557-A1, U.S. Patent Publication No. US-2005-0245795-A1, U.S. Patent Publication No. US-2005-0245795-A1, U.S. Patent Publication No. US-2005-0245795-A1, U.S. Patent Publication No. US-2008-0119703-A1, and U.S. Patent Publication No. US-2008-0108942-A1, each of which is incorporated herein by reference in its entirety.

In one preferred embodiment, a potentiostat is operably connected to the electrode(s) (such as described elsewhere herein), which biases the sensor to enable measurement of a current signal indicative of the analyte concentration in the host (also referred to as the analog portion). In some embodiments, the potentiostat includes a resistor that translates the current into voltage. In some alternative embodiments, a current to frequency converter is provided that is configured to continuously integrate the measured current, for example, using a charge counting device. In some embodiments, the electronics include an A/D converter that digitizes the analog signal into a digital signal, also referred to as 'counts' for processing. Accordingly, the resulting raw data stream in counts, also referred to as raw sensor data, is directly related to the current measured by the potentiostat.

In general, the electronics include a processor module that includes the central control unit that controls the processing of the sensor system. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing or replacement of signal artifacts such as is described in U.S. Patent Publication No. US-2005-0043598-A1). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like.

In some embodiments, the processor module comprises a digital filter, for example, an infinite impulse response (IIR) or finite impulse response (FIR) filter, configured to smooth the raw data stream. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter.

In some embodiments, the processor module is configured to build the data packet for transmission to an outside source, for example, an RF transmission to a receiver. Generally, the data packet comprises a plurality of bits that can include a preamble, a unique identifier identifying the electronics unit, the receiver, or both, (e.g. sensor ID code), data (e.g. raw data, filtered data, or an integrated value) or error detection or correction. Preferably, the data (transmission) packet has a length of from about 8 bits to about 128 bits, preferably about 48 bits; however, larger or smaller packets can be desirable in certain embodiments. The processor module can be configured to transmit any combination of raw or filtered data. In one exemplary embodiment, the transmission packet contains a fixed preamble, a unique ID of the electronics unit, a single five-minute average (e.g. integrated) sensor data value, and a cyclic redundancy code (CRC).

In some embodiments, the processor further performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, and the like. In such cases, the processor includes hardware and software that performs the processing described herein, for example flash memory provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing. Alternatively, some portion of the data processing (such as described with reference to the processor elsewhere herein) can be accomplished at another (e.g. remote) processor and can be configured to be in wired or wireless connection therewith.

In some embodiments, an output module, which is integral with or operatively connected with the processor, includes programming for generating output based on the data stream received from the sensor system and it's processing incurred in the processor. In some embodiments, output is generated via a user interface.

Noise

Generally, implantable sensors measure a signal related to an analyte of interest in a host. For example, an electrochemical sensor can measure glucose, creatinine, or urea in a host, such as an animal (e.g. a human). Generally, the signal is converted mathematically to a numeric value indicative of analyte status, such as analyte concentration, as described in more detail elsewhere herein. In general, the signal generated by conventional analyte sensors contains some noise. Noise is clinically important because it can induce error and can reduce sensor performance, such as by providing a signal that causes the analyte concentration to appear higher or lower than the actual analyte concentration. For example, upward or high noise (e.g. noise that causes the signal to increase) can cause the reading of the host's glucose concentration to appear higher than the actual value, which in turn can lead to improper treatment decisions. Similarly, downward or low noise (e.g. noise that causes the signal to decrease) can cause the reading of the host's glucose concentration to appear lower than its actual value, which in turn can also lead to improper treatment decisions. Accordingly, noise reduction is desirable.

In general, the signal detected by the sensor can be broken down into its component parts. For example, in an enzymatic electrochemical analyte sensor, preferably after sensor break-in is complete, the total signal can be divided into an 'analyte component,' which is representative of analyte (e.g., glucose) concentration, and a 'noise component,' which is caused by non-analyte-related species that have a redox potential that substantially overlaps with the redox potential of the analyte (or measured species, e.g. $H_2O_2$) at an applied voltage. The noise component can be further divided into its component parts, e.g. constant and non-constant noise. It is not unusual for a sensor to experience a certain level of noise. In general, 'constant noise' (sometimes referred to as constant background or baseline) is caused by non-analyte-related factors that are relatively stable over time, including but not limited to electroactive species that arise from generally constant (e.g. daily) metabolic processes. Constant noise can vary widely between hosts. In contrast, 'non-constant noise' (sometimes referred to as non-constant background) is generally caused by non-constant, non-analyte-related species (e.g. non-constant noise-causing electroactive species) that may arise during transient events, such as during host metabolic processes (e.g. wound healing or in response to an illness), or due to ingestion of certain compounds (e.g. certain drugs). In some circumstances, noise can be caused by a variety of noise-causing electroactive species, which are discussed in detail elsewhere herein.

Figure 3:
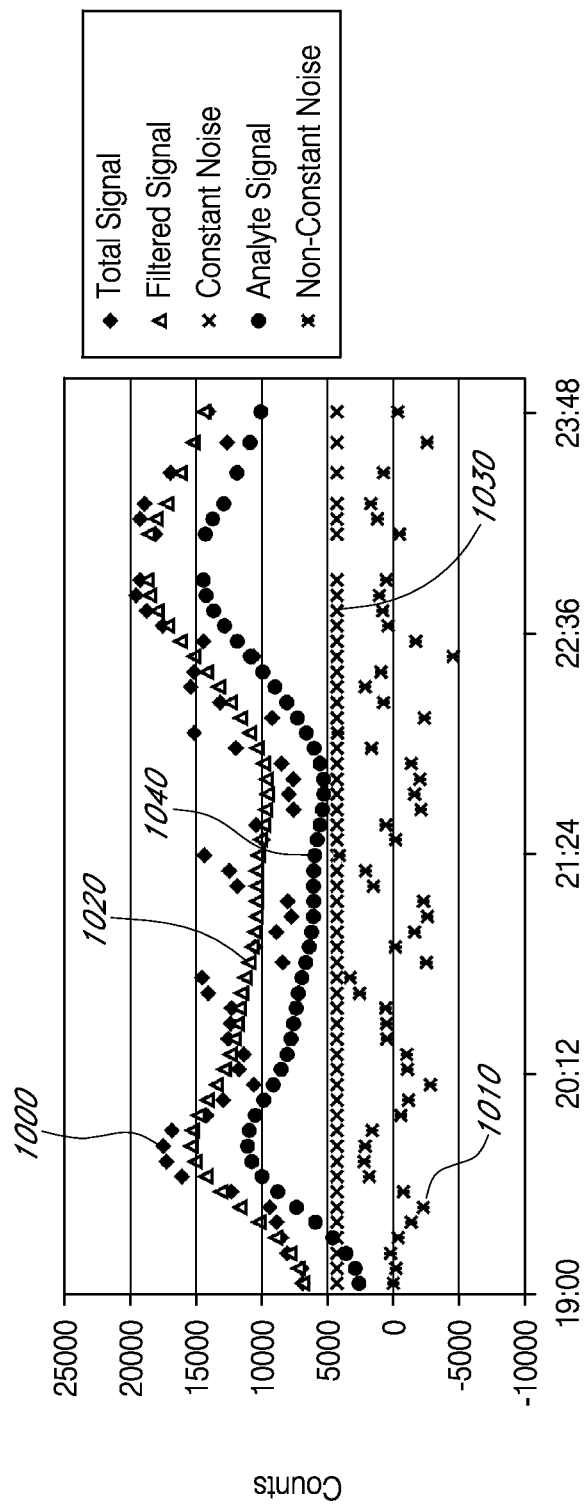
FIG. 3 is a graph illustrating the components of a prior art signal measured by a glucose sensor (after sensor break-in was complete), in a non-diabetic volunteer host.

FIG. 3 is a graph illustrating the components of a signal measured by a transcutaneous glucose sensor (after sensor break-in was complete), in a non-diabetic volunteer host. The Y-axis indicates the signal amplitude (in counts) detected by the sensor. The total signal collected by the sensor is represented by line 1000, which includes components related to glucose, constant noise, and non-constant noise, which are described in more detail elsewhere herein. In some embodiments, the total signal is a raw data stream, which can include an averaged or integrated signal, for example, using a charge-counting device.

The non-constant noise component of the total signal is represented by line 1010. The non-constant noise component 1010 of the total signal 1000 can be obtained by filtering the total signal 1000 to obtain a filtered signal 1020 using any of a variety of known filtering techniques, and then subtracting the filtered signal 1020 from the total signal 1000. In some embodiments, the total signal can be filtered using linear regression analysis of the n (e.g. 10) most recent sampled sensor values. In some embodiments, the total signal can be filtered using non-linear regression. In some embodiments, the total signal can be filtered using a trimmed regression, which is a linear regression of a trimmed mean (e.g., after rejecting wide excursions of any point from the regression line). In this embodiment, after the sensor records glucose measurements at a predetermined sampling rate (e.g., every 30 seconds), the sensor calculates a trimmed mean (e.g., removes highest and lowest measurements from a data set) and then regresses the remaining measurements to estimate the glucose value. In some embodiments, the total signal can be filtered using a non-recursive filter, such as a finite impulse response (FIR) filter. An FIR filter is a digital signal filter, in which every sample of output is the weighted sum of past and current samples of input, using only some finite number of past samples. In some embodiments, the total signal can be filtered using a recursive filter, such as an infinite impulse response (IIR) filter. An IIR filter is a type of digital signal filter, in which every sample of output is the weighted sum of past and current samples of input. In some embodiments, the total signal can be filtered using a maximum-average (max-average) filtering algorithm, which smoothes data based on the discovery that the substantial majority of signal artifacts observed after implantation of glucose sensors in humans, for example, is not distributed evenly above and below the actual blood glucose levels. It has been observed that many data sets are actually characterized by extended periods in which the noise appears to trend downwardly from maximum values with occasional high spikes. To overcome these downward trending signal artifacts, the max-average calculation tracks with the highest sensor values, and discards the bulk of the lower values. Additionally, the max-average method is designed to reduce the contamination of the data with unphysiologically high data from the high spikes. The max-average calculation smoothes data at a sampling interval (e.g. every 30 seconds) for transmission to the receiver at a less frequent transmission interval (e.g. every 5 minutes), to minimize the effects of low non-physiological data. First, the microprocessor finds and stores a maximum sensor counts value in a first set of sampled data points (e.g. 5 consecutive, accepted, thirty-second data points). A frame shift time window finds a maximum sensor counts value for each set of sampled data (e.g. each 5-point cycle length) and stores each maximum value. The microprocessor then computes a rolling average (e.g. 5-point average) of these maxima for each sampling interval (e.g. every 30 seconds) and stores these data. Periodically (e.g. every $10^{th}$ interval), the sensor outputs to the receiver the current maximum of the rolling average (e.g. over the last 10 thirty-second intervals as a smoothed value for that time period (e.g. 5 minutes). In some embodiments, the total signal can be filtered using a 'Cone of Possibility Replacement Method,' which utilizes physiological information along with glucose signal values in order define a 'cone' of physiologically feasible glucose signal values within a human. Particularly, physiological information depends upon the physiological parameters obtained from continuous studies in the literature as well as our own observations. A first physiological parameter uses a maximal sustained rate of change of glucose in humans (e.g. about 4 to 6 mg/dl/min) and a maximum sustained acceleration of that rate of change (e.g. about 0.1 to 0.2 mg/min/min). A second physiological parameter uses the knowledge that rate of change of glucose is lowest at the maxima and minima, which are the areas of greatest risk in patient treatment. A third physiological parameter uses the fact that the best solution for the shape of the curve at any point along the curve over a certain time period (e.g. about 20-25 minutes) is a straight line. It is noted that the maximum rate of change can be narrowed in some instances. Therefore, additional physiological data can be used to modify the limits imposed upon the Cone of Possibility Replacement Method for sensor glucose values. For example, the maximum per minute rate of change can be lower when the subject is lying down or sleeping; on the other hand, the maximum per minute rate change can be higher when the subject is exercising, for example. In some embodiments, the total signal can be filtered using reference changes in electrode potential to estimate glucose sensor data during positive detection of signal artifacts from an electrochemical glucose sensor, the method hereinafter referred to as reference drift replacement; in this embodiment, the electrochemical glucose sensor comprises working, counter, and reference electrodes. This method exploits the function of the reference electrode as it drifts to compensate for counter electrode limitations during oxygen deficits, pH changes, or temperature changes. In alternative implementations of the reference drift method, a variety of algorithms can therefore be implemented based on the changes measured in the reference electrode. Linear algorithms, and the like, are suitable for interpreting the direct relationship between reference electrode drift and the non-glucose rate limiting signal noise such that appropriate conversion to signal noise compensation can be derived. Additional description of signal filtering can be found in U.S. Patent Publication No. US-2005-0043598-A1.

The constant noise signal component 1030 can be obtained by calibrating the sensor signal using reference data, such as one or more blood glucose values obtained from a hand-held blood glucose meter, or the like, from which the baseline 'b' of a regression can be obtained, representing the constant noise signal component 1030.

The analyte signal component 1040 can be obtained by subtracting the constant noise signal component 1030 from the filtered signal 1020.

In general, non-constant noise is caused by interfering species (non-constant noise-causing species), which can be compounds, such as drugs that have been administered to the host, or intermittently produced products of various host metabolic processes. Exemplary interferents include but are not limited to a variety of drugs (e.g. acetaminophen), $H_2O2$ from exterior sources (e.g. produced outside the sensor membrane system), and reactive metabolic species (e.g. reactive oxygen and nitrogen species, some hormones, etc.). Some known interfering species for a glucose sensor include but are not limited to acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid. It has also been observed that non-constant noise may increase when a host is intermittently sedentary, such as when sleeping or sitting for extended periods. This noise may dissipate upon renewed activity by the host. Additional description of this effect can be found in U.S. Patent Publication No. US-2009-0247856-A1.

Interferents

Interferents are molecules or other species that may cause a sensor to generate a false positive or negative analyte signal (e.g. a non-analyte-related signal). Some interferents are known to become reduced or oxidized at the electrochemically reactive surfaces of the sensor, while other interferents are known to interfere with the ability of the enzyme (e.g. glucose oxidase) used to react with the analyte being measured. Yet other interferents are known to react with the enzyme (e.g. glucose oxidase) to produce a byproduct that is electrochemically active. Interferents can exaggerate or mask the response signal, thereby leading to false or misleading results. For example, a false positive signal may cause the host's analyte concentration (e.g., glucose concentration) to appear higher than the true analyte concentration. False-positive signals may pose a clinically significant problem in some conventional sensors. For example in a severe hypoglycemic situation, in which the host has ingested an interferent (e.g. acetaminophen), the resulting artificially high glucose signal can lead the host to believe that he is euglycemic or hyperglycemic. In response, the host may make inappropriate treatment decisions, such as by injecting himself with too much insulin, or by taking no action, when the proper course of action would be to begin eating. In turn, this inappropriate action or inaction may lead to a dangerous hypoglycemic episode for the host. Accordingly, certain embodiments contemplated herein include a membrane system that substantially reduces or eliminates the effects of interferents on analyte measurements. These membrane systems may include one or more domains capable of blocking or substantially reducing the flow of interferents onto the electroactive surfaces of the electrode may reduce noise and improve sensor accuracy as described in more detail in U.S. Patent Publication No. US-2009-0247856-A1.

Drift

The term 'drift' as used herein is a broad term, and is to be given its ordinary and customary meaning to a person of ordinary skill in the art (and is not to be limited to a special or customized meaning), and refers without limitation to a change in the sensitivity of a sensor over time. Drift may be driven by a change in permeability of the sensor membrane system, which may be particularly evident in embodiments which use a polyurethane diffusion resistance domain. Without wishing to be bound by theory, it is believed that the change in permeability in such systems arises from the rearrangement of the diffusion resistance domain polyurethane polymer chains to either bring more hydrophilic components to the surface or otherwise rearrange in some way to allow for greater access to hydrophilic polymer components during hydration of the membrane system. Because of this, increasing the speed of hydration or increasing the wettability of the membrane system reduces system drift.

Due to electrostatically induced hydration, polymers and cross-linked coatings of zwitterionic compounds have near instantaneous wetting properties. As discussed in greater detail below, including one or more zwitterionic compounds, precursors or derivatives thereof (such as hydrolyzable cationic esters) in the outermost domain of a membrane system or applying a coating of such compounds to the surface of the membrane system results in reduced sensor drift.

Membrane Fabrication

Preferably, polymers of the preferred embodiments may be processed by solution-based techniques such as spraying, dipping, casting, electrospinning, vapor deposition, spin coating, coating, and the like. Water-based polymer emulsions can be fabricated to form membranes by methods similar to those used for solvent-based materials. In both cases the evaporation of a volatile liquid (e.g. organic solvent or water) leaves behind a film of the polymer. Cross-linking of the deposited film may be performed through the use of multi-functional reactive ingredients by a number of methods well known to those skilled in the art. The liquid system may cure by heat, moisture, high-energy radiation, ultraviolet light, or by completing the reaction, which produces the final polymer in a mold or on a substrate to be coated.

In some embodiments, the wetting property of the membrane (and by extension the extent of sensor drift exhibited by the sensor) can be adjusted and/or controlled by creating covalent cross-links between surface-active group-containing polymers, polymers with zwitterionic groups (or precursors or derivatives thereof), and combinations thereof. Cross-linking can have a substantial effect on film structure, which in turn can affect the film's surface wetting properties.

Cross-linked polymers can have different cross-linking densities. In certain embodiments, cross-linkers are used to promote cross-linking between layers. In other embodiments, in replacement of (or in addition to) the cross-linking techniques described above, heat is used to form cross-linking. For example, in some embodiments imide and amide bonds can be formed between two polymers as a result of high temperature. In some embodiments, photo cross-linking is performed to form covalent bonds between the polycationic layers(s) and polyanionic layer(s). One major advantage to photo-cross-linking is that it offers the possibility of patterning. In certain embodiments, patterning using photo-cross linking is performed to modify the film structure and thus to adjust the wetting property of the membrane.

Domains that include at least two surface-active group-containing polymers may be made using any of the methods of forming polymer blends known in the art. In one exemplary embodiment, a solution of a polyurethane containing silicone end groups is mixed with a solution of a polyurethane containing fluorine end groups (e.g. wherein the solutions include the polymer dissolved in a suitable solvent such as acetone, ethyl alcohol, DMAC, THF, 2-butanone, and the like). The mixture can then be drawn into a film or applied to a surface using any method known in the art (e.g. spraying, painting, dip coating, vapor depositing, molding, 3-D printing, lithographic techniques (e.g. photolithograph), micro- and nano-pipetting printing techniques, etc.). The mixture can then be cured under high temperature (e.g. 50-150° C.). Other suitable curing methods may include ultraviolet or gamma radiation, for example.

In some embodiments, polymer blends used to make any of the domains described herein may be employed which comprise monomers with zwitterionic end groups, or precursors or derivatives thereof. In other embodiments, polymer blends used to make any of the domains described herein may be employed which comprise a polymer with positively charged surface-active groups and a polymer with negatively charged surface-active groups. Polymers prepared from such blends are polyampholytic, and typically have a relatively homogenous nanoscale distribution of like charges across the polymer surface. In some embodiments, polymer blends comprise a relatively equal number of positively charged and negatively charged surface-active groups. Examples of such polymer blends are described in Chen et al., Polymer 2010, 51:5283-93. In other embodiments, polyampholytic blends may comprise positively and negatively charged surface-active groups present at unequal amounts. In some embodiments, a blend may contain more positively charged surface-active groups; while in other embodiments, a blend may contain more negatively charged surface-active groups.

For use in certain devices described herein, polymer blends to make polyampholytic polymers may contain up to 0.1, 0.2, 0.3, 0.4, 0.5, 1, 2, or 5% wt. charged monomers with surface-active groups.

Some amount of cross-linking agent can also be included in the mixture to induce cross-linking between polymer molecules. Non-limiting examples of suitable cross-linking agents include isocyanate, carbodiimide, gluteraldehyde or other aldehydes, epoxy, acrylates, free-radical based agents, ethylene glycol diglycidyl ether (EGDE), poly(ethylene glycol) diglycidyl ether (PEGDE), or dicumyl peroxide (DCP). In one embodiment, from about 0.1% to about 15% w/w of cross-linking agent is added relative to the total dry weights of cross-linking agent and polymers added when blending the ingredients (in one example, about 1% to about 10%). During the curing process, substantially all of the cross-linking agent is believed to react, leaving substantially no detectable unreacted cross-linking agent in the final film.

Bioprotective Domain

The bioprotective domain is the domain or layer of an implantable device configured to interface with (e.g. contact) a biological fluid when implanted in a host or connected to the host (e.g. via an intravascular access device providing extracorporeal access to a blood vessel). The noise reducing capacity of certain bioprotective domains is described in more detail in U.S. Patent Publication No. US-2009-0247856-A1.

Some embodiments described herein may include membranes which comprise a bioprotective domain 46 (see FIGS. 2A-2C), also referred to as a bioprotective layer, including at least one polymer containing a surface-active group. In some embodiments, the surface-active group-containing polymer is a surface-active end group-containing polymer. In some of these embodiments, the surface-active end group-containing polymer is a polymer having covalently bonded surface-active end groups. However, it is contemplated that other surface-active group-containing polymers may also be used and can be formed by modification of fully-reacted base polymers via the grafting of side chain structures, surface treatments or coatings applied after membrane fabrication (e.g., via surface-modifying additives), blending of a surface-modifying additive to a base polymer before membrane fabrication, immobilization of the surface-active-group-containing soft segments by physical entrainment during synthesis, or the like. Certain exemplary bioprotective domains which may be used in some embodiments as described herein are described in more detail in U.S. Patent Publication No. US-2009-0247856-A1. In some embodiments, the surface active end groups are zwitterionic, or precursors or derivatives thereof. In some embodiments, the surface-active end groups are suitable to cross-link to zwitterionic compounds, precursors, or derivatives thereof.

Base polymers useful for certain embodiments may include any linear or branched polymer on the backbone structure of the polymer. Suitable base polymers may include, but are not limited to, epoxies, polyolefins, polysiloxanes, polyethers, acrylics, polyesters, carbonates, and polyurethanes, wherein polyurethanes may include polyurethane copolymers such as polyether-urethane-urea, polycarbonate-urethane, polyether-urethane, silicone-polyether-urethane, silicone-polycarbonate-urethane, polyester-urethane, and the like. In some embodiments, base polymers may be selected for their bulk properties, such as, but not limited to, tensile strength, flex life, modulus, and the like. For example, polyurethanes are known to be relatively strong and to provide numerous reactive pathways, which properties may be advantageous as bulk properties for a membrane domain of the continuous sensor.

In some embodiments, a base polymer synthesized to have hydrophilic segments may be used to form the bioprotective layer. For example, a linear base polymer including biocompatible segmented block polyurethane copolymers comprising hard and soft segments may be used. In some embodiments, the hard segment of the copolymer may have a molecular weight of from about 160 daltons to about 10,000 daltons, and sometimes from about 200 daltons to about 2,000 daltons. In some embodiments, the molecular weight of the soft segment may be from about 200 daltons to about 10,000,000 daltons, and sometimes from about 500 daltons to about 5,000,000 daltons, and sometimes from about 500,00 daltons to about 2,000,000 daltons. It is contemplated that polyisocyanates used for the preparation of the hard segments of the copolymer may be aromatic or aliphatic diisocyanates. The soft segments used in the preparation of the polyurethane may be a polyfunctional aliphatic polyol, a polyfunctional aliphatic or aromatic amine, or the like that may be useful for creating permeability of the analyte (e.g. glucose) therethrough, and may include, for example, polyvinyl acetate (PVA), poly(ethylene glycol) (PEG), polyacrylamide, acetates, polyethylene oxide (PEO), polyethylacrylate (PEA), polyvinylpyrrolidone (PVP), and variations thereof (e.g. PVP vinyl acetate), and wherein PVP and variations thereof may be preferred for their hydrolytic stability in some embodiments.

Alternatively, in some embodiments, the bioprotective layer may comprise a combination of a base polymer (e.g. polyurethane) and one or more hydrophilic polymers, such as, PVA, PEG, polyacrylamide, acetates, PEO, PEA, PVP, and variations thereof (e.g. PVP vinyl acetate), e.g. as a physical blend or admixture wherein each polymer maintains its unique chemical nature. It is contemplated that any of a variety of combination of polymers may be used to yield a blend with desired glucose, oxygen, and interference permeability properties. For example, in some embodiments, the bioprotective layer may be formed from a blend of a polycarbonate-urethane base polymer and PVP, but in other embodiments, a blend of a polyurethane, or another base polymer, and one or more hydrophilic polymers may be used instead. In some of the embodiments involving use of PVP, the PVP portion of the polymer blend may comprise from about 5% to about 50% by weight of the polymer blend, sometimes from about 15% to 20%, and other times from about 25% to 40%. It is contemplated that PVP of various molecular weights may be used. For example, in some embodiments, the molecular weight of the PVP used may be from about 25,000 daltons to about 5,000,000 daltons, sometimes from about 50,000 daltons to about 2,000,000 daltons, and other times from 6,000,000 daltons to about 10,000,000 daltons.

The term 'surface-active group' and 'surface-active end group' as used herein are broad terms and are used in their ordinary sense, including, without limitation, surface-active oligomers or other surface-active moieties having surface-active properties, such as alkyl groups, which preferentially migrate towards a surface of a membrane formed there from. Surface-active groups preferentially migrate toward air (e.g., driven by thermodynamic properties during membrane formation). In some embodiments, the surface-active groups are covalently bonded to the base polymer during synthesis. In some preferred embodiments, surface-active groups may include silicone, sulfonate, fluorine, polyethylene oxide, hydrocarbon groups, zwitterionic groups, charged groups, and the like. The surface activity (e.g., chemistry, properties) of a membrane domain including a surface-active group-containing polymer reflects the surface activity of the surface-active groups rather than that of the base polymer. In other words, surface-active groups control the chemistry at the surface (e.g., the biological contacting surface) of the membrane without compromising the bulk properties of the base polymer. The surface-active groups of the preferred embodiments are selected for desirable surface properties, for example, non-constant noise-blocking ability, break-in time (reduced), ability to repel charged species, cationic or anionic blocking, or the like. In some preferred embodiments, the surface-active groups are located on one or more ends of the polymer backbone, and referred to as surface-active end groups, wherein the surface-active end groups are believed to more readily migrate to the surface of the bioprotective domain/layer formed from the surface-active group-containing polymer in some circumstances.

In some embodiments, the bioprotective domain 46 is formed from a polymer containing silicone as the surface-active group, for example, a polyurethane containing silicone end group(s). Some embodiments include a continuous analyte sensor configured for insertion into a host, wherein the sensor has a membrane located over the sensing mechanism, which includes a polyurethane comprising silicone end groups configured to substantially block the effect of non-constant noise-causing species on the sensor signal, as described in more detail elsewhere herein. In some embodiments, the polymer includes about 10%, 11%, 12%, 13%, 14%, 15%, 16%, 17%, 18%, 19%, 20%, 21%, 22%, 23%, 24%, 25%, 26%, 27%, 28%, 29%, 30%, to about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% or 55% silicone by weight. In certain embodiments, the silicone (e.g. a precursor such as PDMS) has a molecular weight from about 500 to about 10,000 daltons, preferably at least about 200 daltons. In some embodiments, the base polymer includes at least about 10% silicone by weight, and preferably from about 19% to about 40% silicone by weight. These ranges are described in U.S. Patent Publication No. US-2009-0247856-A1 as providing an advantageous balance of noise-reducing functionality, while maintaining sufficient glucose permeability in embodiments wherein the sensor is a glucose sensor, for example.

In some embodiments, the bioprotective domain is formed from a polymer containing fluorine as a surface-active group, for example, a polyurethane that contains a fluorine end groups. In preferred embodiments, the polymer includes from about 1% to about 25% fluorine by weight. Some embodiments include a continuous analyte sensor configured for insertion into a host, wherein the sensor has a membrane located over the sensing mechanism, wherein the membrane includes a polyurethane containing fluorine surface-active groups, and wherein the membrane is configured and arranged to reduce a break-in time of a sensor as compared to a membrane formed from a similar base polymer without the surface-active group(s). For example, in preferred embodiments, a glucose sensor having a bioprotective domain of the preferred embodiments has a response time (e.g. $t_{90}$) of less than 120 seconds, sometimes less than 60 seconds, and sometimes less than about 45, 30, 20, or 10 seconds (across a physiological range of glucose concentration).

In some embodiments, the bioprotective domain may be formed from a polymer that contains sulfonate as a surface-active group, for example, a polyurethane containing sulfonate end group(s). In some embodiments, the continuous analyte sensor configured for insertion into a host may include a membrane located over the sensing mechanism, wherein the membrane includes a polymer that contains sulfonate as a surface-active group, and is configured to repel charged species, for example, due to the net negative charge of the sulfonated groups.

In some embodiments, a blend of two or more (e.g. two, three, four, five, or more) surface-active group-containing polymers is used to form a bioprotective membrane domain. For example, by blending a polyurethane with silicone end groups and a polyurethane with fluorine end groups, and forming a bioprotective membrane domain from that blend, a sensor can be configured to substantially block non-constant noise-causing species and reduce the sensor's $t_{90}$, as described in more detail elsewhere herein. Similarly, by blending a polyurethane containing silicone end groups, a polyurethane containing fluorine end groups, and a polyurethane containing sulfonate end groups, and forming a bioprotective membrane domain from that blend, a sensor can be configured to substantially block non-constant noise-causing species, to reduce the sensor's break-in time and to repel charged species, as described in more detail above.

In some embodiments, one of the two or more surface-active end group-containing polymers comprises zwitterionic surface-active end groups, or precursors or derivatives thereof. In these embodiments, it is intended that at least a portion of the zwitterionic surface-active end groups, or precursors or derivatives thereof, exist as zwitterionic surface-active end groups while the device is in vivo. As such, these end-groups present mixed charged areas of the device surface to the surrounding environment, thereby increasing surface hydration of the device, and potentially reducing nonspecific protein adsorption and cell adhesion.

In other embodiments, the blend of two or more surface-active group-containing polymers comprises one surface-active group that is negatively charged and one surface-active group that is positively charged. In some embodiments, the number of negatively and positively charged surface-active groups is approximately equal. That is, the surface of a bioprotective membrane domain formed from such a blend is about net neutrally charged. However, the negatively and positively charged surface-active end groups are preferably homogenously dispersed throughout the surface of the domain, thus providing a mixed-charge device surface which increases surface hydration of the device in vivo, and potentially reduces nonspecific protein adsorption and cell adhesion. In other embodiments, the number of negatively and positively charged surface-active groups is unequal. In some related embodiments, the blend contains more positively charged surface-active groups than negatively charged surface-active groups. Alternatively, the blend may contain more negatively charged surface-active groups than positively charged surface-active groups.

Although in some embodiments, blending of two or more surface-active group-containing polymers is used, in other embodiments, a single component polymer can be formed by synthesizing two or more surface-active groups with a base polymer to achieve similarly advantageous surface properties; however, blending may be preferred in some embodiments for ease of manufacture.

In some embodiments, the bioprotective domain 46 is positioned most distally to the sensing region such that its outer most domain contacts a biological fluid when inserted in vivo. In some embodiments, the bioprotective domain is resistant to cellular attachment, impermeable to cells, and may be composed of a biostable material. While not wishing to be bound by theory, it is believed that when the bioprotective domain 46 is resistant to cellular attachment (for example, attachment by inflammatory cells, such as macrophages, which are therefore kept a sufficient distance from other domains, for example, the enzyme domain), hypochlorite and other oxidizing species are short-lived chemical species in vivo and biodegradation does not generally occur. Additionally, the materials preferred for forming the bioprotective domain 46 may be resistant to the effects of these oxidative species and have thus been termed biodurable. In some embodiments, the bioprotective domain controls the flux of oxygen and other analytes (for example, glucose) to the underlying enzyme domain (e.g. wherein the functionality of the diffusion resistance domain is built-into the bioprotective domain such that a separate diffusion resistance domain is not required).

In some embodiments, one or more zwitterionic compounds, precursors or derivatives thereof, preferably a betaine compound such as a carboxyl, sulfo, or phosphor betaine compound, precursor or derivative thereof (for example alkylbetaines or aminobetaines), may be incorporated into the bioprotective domain, for example up to about 0.1, 0.2, 0.3, 0.4, 0.5, 1, 2, or 5% by weight of the bioprotective domain. Exemplary betaines include cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), and poly(sulfobetaine) (pSB). It will be appreciated that many more zwitterionic compounds or precursors or derivatives thereof may be applicable and that this list of exemplary betaines is not intended to limit the scope of the embodiments.

Zwitterionic compounds, precursors or derivatives thereof may be incorporated into the bioprotective domain surface-active groups in one or more polymers used in preparation of the domain. In this regard, the charged surface-active groups "bloom" or migrate to the surface of the domain, thus presenting a surface with mixed charge surface-active groups for contact with a biological fluid.

In other embodiments, the bioprotective domain is prepared from a polymer blend comprising positively charged surface-active groups and negatively charged surface-active groups. Like the zwitterionic surface-active groups described above, the positively and negatively charged surface-active groups migrate to the surface of the domain, and result in substantially homogenous dispersion of like-charged groups at the surface.

In embodiments where there are relatively even amounts of positively and negatively charged monomers, the resulting bioprotective domain surface preferably provides a mixed-charge device surface (resulting from the presence of both positively and negatively charged surface-active groups). This surface has the benefits of increased surface hydration of the device in vivo, and potentially reduction of nonspecific protein adsorption and cell adhesion.

In other embodiments, the number of negatively and positively charged surface-active groups is unequal. In some related embodiments, the blend contains more positively charged surface-active groups than negatively charged surface-active groups. Alternatively, the blend may contain more negatively charged surface-active groups than positively charged surface-active groups. In either case, the resulting surfaces may similarly exhibit increased surface hydration of the device in vivo and potentially reduction of nonspecific protein adsorption and cell adhesion, and may also be configured to substantially block non-constant noise-causing species, or to repel charged species.

In other embodiments, one or more zwitterionic compounds or precursors or derivatives thereof may be applied to the outermost surface of the membrane system as a coating or surface treatment. In some embodiments, the coating or surface treatment is cross-linkable to the outermost domain of the membrane system. In these embodiments, the outermost domain of the membrane system will typically comprise surface-active groups that are suitable for cross-linking to the zwitterionic compounds or precursors or derivatives thereof. In some embodiments, the coating or surface treatment is polymeric. In some alternate embodiments, the coating or surface treatment is not polymeric. In some embodiments, the coating or surface treatment may be a hydrogel comprising a zwitterionic compound or precursor or derivative thereof. Alternatively, in some embodiments, the zwitterionic compound or precursor or derivative thereof is not incorporated into a hydrogel for inclusion in or application to the membrane system.

In some embodiments, the one or more zwitterionic compounds or precursors or derivatives thereof applied to the surface of the membrane system are hydrolyzable cationic esters of zwitterionic compounds. In these embodiments, the hydrolyzable cationic esters provide the added benefit that hydrolysis of the cationic esters into nonfouling zwitterionic groups can kill microbes (such as bacteria) or condense DNA. Further, the mixed-charge nature of the resulting zwitterionic groups result in inhibition of nonspecific protein adsorption on the surface of the sensors. In these embodiments, cationic betaine esters, such as cationic pCB esters are preferable.

In certain embodiments, the thickness of the bioprotective domain may be from about 0.1, 0.5, 1, 2, 4, 6, 8 microns or less to about 10, 15, 20, 30, 40, 50, 75, 100, 125, 150, 175, 200 or 250 microns or more. In some of these embodiments, the thickness of the bioprotective domain may be sometimes from about 1 to about 5 microns, and sometimes from about 2 to about 7 microns. In other embodiments, the bioprotective domain may be from about 20 or 25 microns to about 50, 55, or 60 microns thick. In some embodiments, the glucose sensor may be configured for transcutaneous or short-term subcutaneous implantation, and may have a thickness from about 0.5 microns to about 8 microns, and sometimes from about 4 microns to about 6 microns. In one glucose sensor configured for fluid communication with a host's circulatory system, the thickness may be from about 1.5 microns to about 25 microns, and sometimes from about 3 to about 15 microns. It is also contemplated that in some embodiments, the bioprotective layer or any other layer of the electrode may have a thickness that is consistent, but in other embodiments, the thickness may vary. For example, in some embodiments, the thickness of the bioprotective layer may vary along the longitudinal axis of the electrode end.

Diffusion Resistance Domain

In some embodiments, a diffusion resistance domain 44, also referred to as a diffusion resistance layer, may be used and is situated more proximal to the implantable device relative to the bioprotective domain. In some embodiments, the functionality of the diffusion resistance domain may be built into the bioprotective domain that comprises the surface-active group-containing base polymer. Accordingly, it is to be noted that the description herein of the diffusion resistance domain may also apply to the bioprotective domain. The diffusion resistance domain serves to control the flux of oxygen and other analytes (for example, glucose) to the underlying enzyme domain. As described in more detail elsewhere herein, there exists a molar excess of glucose relative to the amount of oxygen in blood, i.e., for every free oxygen molecule in extracellular fluid, there are typically more than 100 glucose molecules present (see Updike et al., Diabetes Care 5:207-21 (1982)). However, an immobilized enzyme-based sensor employing oxygen as cofactor is supplied with oxygen in non-rate-limiting excess in order to respond linearly to changes in glucose concentration, while not responding to changes in oxygen tension. More specifically, when a glucose-monitoring reaction is oxygen-limited, linearity is not achieved above minimal concentrations of glucose. Without a semipermeable membrane situated over the enzyme domain to control the flux of glucose and oxygen, a linear response to glucose levels can be obtained only up to about 40 mg/dL. However, in a clinical setting, a linear response to glucose levels is desirable up to at least about 500 mg/dL.

The diffusion resistance domain 44 includes a semipermeable membrane that controls the flux of oxygen and glucose to the underlying enzyme domain 42, preferably rendering oxygen in non-rate-limiting excess. As a result, the upper limit of linearity of glucose measurement is extended to a much higher value than that which is achieved without the diffusion resistance domain. In some embodiments, the diffusion resistance domain exhibits an oxygen-to-glucose permeability ratio of approximately 200:1, but in other embodiments the oxygen-to-glucose permeability ratio may be approximately 100:1, 125:1, 130:1, 135:1, 150:1, 175:1, 225:1, 250:1, 275:1, 300:1, or 500:1. As a result of the high oxygen-to-glucose permeability ratio, one-dimensional reactant diffusion may provide sufficient excess oxygen at all reasonable glucose and oxygen concentrations found in the subcutaneous matrix (See Rhodes et al., Anal. Chem., 66:1520-1529 (1994)). In some embodiments, a lower ratio of oxygen-to-glucose can be sufficient to provide excess oxygen by using a high oxygen soluble domain (for example, a silicone material) to enhance the supply/transport of oxygen to the enzyme membrane or electroactive surfaces. By enhancing the oxygen supply through the use of a silicone composition, for example, glucose concentration can be less of a limiting factor. In other words, if more oxygen is supplied to the enzyme or electroactive surfaces, then more glucose can also be supplied to the enzyme without creating an oxygen rate-limiting excess.

In some embodiments, the diffusion resistance domain is formed of a base polymer synthesized to include a polyurethane membrane with both hydrophilic and hydrophobic regions to control the diffusion of glucose and oxygen to an analyte sensor. A suitable hydrophobic polymer component may be a polyurethane or polyether urethane urea. Polyurethane is a polymer produced by the condensation reaction of a diisocyanate and a difunctional hydroxyl-containing material. A polyurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the diffusion resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In one embodiment of a polyurethane-based resistance domain, the hydrophilic polymer component is polyethylene oxide. For example, one useful hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

Alternatively, in some embodiments, the resistance domain may comprise a combination of a base polymer (e.g. polyurethane) and one or more hydrophilic polymers (e.g. PVA, PEG, polyacrylamide, acetates, PEO, PEA, PVP, and variations thereof). It is contemplated that any of a variety of combination of polymers may be used to yield a blend with desired glucose, oxygen, and interference permeability properties. For example, in some embodiments, the resistance domain may be formed from a blend of a silicone polycarbonate-urethane base polymer and a PVP hydrophilic polymer, but in other embodiments, a blend of a polyurethane, or another base polymer, and one or more hydrophilic polymers may be used instead. In some of the embodiments involving the use of PVP, the PVP portion of the polymer blend may comprise from about 5% to about 50% by weight of the polymer blend, sometimes from about 15% to 20%, and other times from about 25% to 40%. It is contemplated that PVP of various molecular weights may be used. For example, in some embodiments, the molecular weight of the PVP used may be from about 25,000 daltons to about 5,000,000 daltons, sometimes from about 50,000 daltons to about 2,000,000 daltons, and other times from 6,000,000 daltons to about 10,000,000 daltons.

In some embodiments, the diffusion resistance domain 44 can be formed as a unitary structure with the bioprotective domain 46; that is, the inherent properties of the diffusion resistance domain 44 are incorporated into bioprotective domain 46 such that the bioprotective domain 46 functions as a diffusion resistance domain 44.

The diffusion resistance domain may comprise one surface-active end group containing polymer, or a blend of two or more (e.g. two, three, four, five, or more) surface-active end group-containing polymers, as described above. For example, in some embodiments the diffusion resistance domain may comprise one surface-active end group containing polymer that comprises surface-active end groups that are zwitterionic, or are precursors or derivatives thereof. In other embodiments, one surface-active group containing polymer in a blend of two or more surface-active group containing polymers comprises zwitterionic surface-active groups, or precursors or derivatives thereof. In other embodiments, a blend may comprise a polymer with positively charged surface-active groups and a polymer with negatively charged surface-active groups.

In some embodiments where the diffusion resistance domain comprises one or more zwitterionic surface-active groups, or precursors or derivatives thereof, the zwitterionic surface-active group may comprise a betaine moiety such as a carboxyl, sulfo, or phosphor betaine group, or precursors or derivatives thereof (for example alkylbetaines or aminobetaines), for example up to about 0.1, 0.2, 0.5, 1, 2, or 5% wt. of the domain. Exemplary betaines include cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), and poly(sulfobetaine) (pSB). It will be appreciated that many more zwitterionic groups, or precursors or derivatives thereof, may be applicable and that this list of exemplary betaines is not intended to limit the scope of the embodiments. In some embodiments, hydrolyzable cationic esters of zwitterionic groups (as discussed elsewhere) may be used at similar concentrations for incorporation into the diffusion resistance domain.

In some other embodiments, a blend of two or more surface-active group-containing polymers comprises one surface-active group that is negatively charged and one surface-active group that is positively charged. In these embodiments, the negatively and positively charged surface-active groups are preferably homogenously distributed throughout the surface of the domain thus providing a mixed-charge domain surface. In some embodiments, the number of negatively and positively charged surface-active groups is such that a diffusion resistance domain formed from the blend is about net neutrally charged. In other embodiments, the number of positively charged and negatively charged surface-active groups may be unequal, with either more positively charged or negatively charged surface-active groups being present.

In certain embodiments, the thickness of the resistance domain may be from about 0.05 microns or less to about 200 microns or more. In some of these embodiments, the thickness of the resistance domain may be from about 0.05, 0.1, 0.15, 0.2, 0.25, 0.3, 0.35, 0.4, 0.45, 0.5, 1, 1.5, 2, 2.5, 3, 3.5, 4, 6, 8 microns to about 9, 10, 11, 12, 13, 14, 15, 16, 17, 18, 19, 19.5, 20, 30, 40, 50, 60, 70, 75, 80, 85, 90, 95, or 100 microns. In some embodiments, the thickness of the resistance domain is from about 2, 2.5 or 3 microns to about 3.5, 4, 4.5, or 5 microns in the case of a transcutaneously implanted sensor or from about 20 or 25 microns to about 40 or 50 microns in the case of a wholly implanted sensor.

Enzyme Domain

In some embodiments, an enzyme domain 42, also referred to as the enzyme layer, may be used and is situated less distal from the electrochemically reactive surfaces than the diffusion resistance domain 44. The enzyme domain comprises a catalyst configured to react with an analyte. In one embodiment, the enzyme domain is an immobilized enzyme domain 42 including glucose oxidase. In other embodiments, the enzyme domain 42 can be impregnated with other oxidases, for example, galactose oxidase, cholesterol oxidase, amino acid oxidase, alcohol oxidase, lactate oxidase, or uricase. For example, for an enzyme-based electrochemical glucose sensor to perform well, the sensor's response should neither be limited by enzyme activity nor cofactor concentration.

The enzyme domain may comprise one surface-active end group containing polymer, or a blend of two or more (e.g. two, three, four, five, or more) surface-active end group-containing polymers, as described above. For example, in some embodiments the enzyme domain may comprise one surface-active end group containing polymer that comprises surface-active end groups that are zwitterionic, or are precursors or derivatives thereof. In other embodiments, one surface-active group containing polymer in a blend of two or more surface-active group containing polymers comprises zwitterionic surface-active groups, or precursors or derivatives thereof. In other embodiments, a blend may comprise a polymer with positively charged surface-active groups and a polymer with negatively charged surface-active groups.

In some embodiments where the enzyme domain comprises one or more zwitterionic surface-active groups, or precursors or derivatives thereof, the zwitterionic surface-active group may comprise a betaine moiety such as a carboxyl, sulfo, or phosphor betaine group, or precursors or derivatives thereof (for example alkylbetaines or aminobetaines), for example up to about 0.1, 0.2, 0.5, 1, 2, or 5% wt. of the domain. Exemplary betaines include cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), and poly(sulfobetaine) (pSB). It will be appreciated that many more zwitterionic groups, or precursors or derivatives thereof, may be applicable and that this list of exemplary betaines is not intended to limit the scope of the embodiments. In some embodiments, hydrolyzable cationic esters of zwitterionic groups (as discussed elsewhere) may be used at similar concentrations for incorporation into the enzyme domain.

In some other embodiments, a blend of two or more surface-active group-containing polymers comprises one surface-active group that is negatively charged and one surface-active group that is positively charged. In some embodiments, the number of negatively and positively charged surface-active groups is such that an enzyme domain formed from the blend is about net neutrally charged. In other embodiments, the number of positively charged and negatively charged surface-active groups may be unequal, with either more positively charged or negatively charged surface-active groups being present.

In some embodiments, the catalyst (enzyme) can be impregnated or otherwise immobilized into the bioprotective or diffusion resistance domain such that a separate enzyme domain 42 is not required (e.g. wherein a unitary domain is provided including the functionality of the bioprotective domain, diffusion resistance domain, and enzyme domain). In some embodiments, the enzyme domain 42 is formed from a polyurethane, for example, aqueous dispersions of colloidal polyurethane polymers including the enzyme.

In some embodiments, the thickness of the enzyme domain may be from about 0.01, 0.05, 0.6, 0.7, or 0.8 microns to about 1, 1.2, 1.4, 1.5, 1.6, 1.8, 2, 2.1, 2.2, 2.5, 3, 4, 5, 10, 20, 30 40, 50, 60, 70, 80, 90, or 100 microns. In more preferred embodiments, the thickness of the enzyme domain is between about 0.05, 0.1, 0.15, 0.2, 0.25, 0.3, 0.35, 0.4, 0.45, 0.5, 1, 1.5, 2, 2.5, 3, 4, or 5 microns and 6, 7, 8, 9, 10, 11, 12, 13, 14, 15, 16, 17, 18, 19, 19.5, 20, 25, or 30 microns. In even more preferred embodiments, the thickness of the enzyme domain is from about 2, 2.5, or 3 microns to about 3.5, 4, 4.5, or 5 microns in the case of a transcutaneously implanted sensor or from about 6, 7, or 8 microns to about 9, 10, 11, or 12 microns in the case of a wholly implanted sensor.

Interference Domain

It is contemplated that in some embodiments, such as the embodiment illustrated in FIG. 2B, an optional interference domain 40, also referred to as the interference layer, may be provided, in addition to the bioprotective domain and the enzyme domain. The interference domain 40 may substantially reduce the permeation of one or more interferents into the electrochemically reactive surfaces. Preferably, the interference domain 40 is configured to be much less permeable to one or more of the interferents than to the measured species. It is also contemplated that in some embodiments, where interferent blocking may be provided by the bioprotective domain (e.g. via a surface-active group-containing polymer of the bioprotective domain), a separate interference domain may not be used.

In some embodiments, the interference domain is formed from a silicone-containing polymer, such as a polyurethane containing silicone, or a silicone polymer. While not wishing to be bound by theory, it is believed that, in order for an enzyme-based glucose sensor to function properly, glucose would not have to permeate the interference layer, where the interference domain is located more proximal to the electroactive surfaces than the enzyme domain. Accordingly, in some embodiments, a silicone-containing interference domain, comprising a greater percentage of silicone by weight than the bioprotective domain, may be used without substantially affecting glucose concentration measurements. For example, in some embodiments, the silicone-containing interference domain may comprise a polymer with a high percentage of silicone (e.g. from about 25%, 30%, 35%, 40%, 45%, or 50% to about 60%, 70%, 80%, 90% or 95%).

In one embodiment, the interference domain may include ionic components incorporated into a polymeric matrix to reduce the permeability of the interference domain to ionic interferents having the same charge as the ionic components. In another embodiment, the interference domain may include a catalyst (for example, peroxidase) for catalyzing a reaction that removes interferents. U.S. Pat. No. 6,413,396 and U.S. Pat. No. 6,565,509 disclose methods and materials for eliminating interfering species.

In some embodiments, the interference domain may comprise one surface-active end group containing polymer, or a blend of two or more (e.g. two, three, four, five, or more) surface-active end group-containing polymers, as described above. For example, in some embodiments the interference domain may comprise one surface-active end group containing polymer that comprises surface-active end groups that are zwitterionic, or are precursors or derivatives thereof. In other embodiments, one surface-active end group-containing polymer in a blend of two or more surface-active end group containing polymers comprises zwitterionic surface-active end groups, or precursors or derivatives thereof. In other embodiments, the interference domain comprises a blend of two or more one surface-active end group containing polymers, wherein one of the polymers in the blend comprises negatively charged surface-active end groups and one of the polymers in the blend comprises positively charged surface-active end groups.

The interference domain may comprise one surface-active end group containing polymer, or a blend of two or more (e.g. two, three, four, five, or more) surface-active end group-containing polymers, as described above. For example, in some embodiments the interference domain may comprise one surface-active end group containing polymer that comprises surface-active end groups that are zwitterionic, or are precursors or derivatives thereof. In other embodiments, one surface-active group containing polymer in a blend of two or more surface-active group containing polymers comprises zwitterionic surface-active groups, or precursors or derivatives thereof. In other embodiments, a blend may comprise a polymer with positively charged surface-active groups and a polymer with negatively charged surface-active groups.

In some embodiments where the interference domain comprises one or more zwitterionic surface-active groups, or precursors or derivatives thereof, the zwitterionic surface-active group may comprise a betaine moiety such as a carboxyl, sulfo, or phosphor betaine group, or precursors or derivatives thereof (for example alkylbetaines or aminobetaines), for example up to about 0.1, 0.2, 0.5, 1, 2, or 5% wt. of the domain. Exemplary betaines include cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), and poly (sulfobetaine) (pSB). It will be appreciated that many more zwitterionic groups, or precursors or derivatives thereof, may be applicable and that this list of exemplary betaines is not intended to limit the scope of the embodiments. In some embodiments, hydrolyzable cationic esters of zwitterionic groups (as discussed elsewhere) may be used at similar concentrations for incorporation into the interference domain.

In some other embodiments, a blend of two or more surface-active group-containing polymers comprises one surface-active group that is negatively charged and one surface-active group that is positively charged. In some embodiments, the number of negatively and positively charged surface-active groups is such that an interference domain formed from the blend is about net neutrally charged. In other embodiments, the number of positively charged and negatively charged surface-active groups may be unequal, with either more positively charged or negatively charged surface-active groups being present.

In certain embodiments, the interference domain may include a thin membrane that is designed to limit diffusion of certain species, for example, those greater than 34,000 daltons in molecular weight. In these embodiments, the interference domain permits certain substances (for example, hydrogen peroxide) that are to be measured by the electrodes to pass through, and prevents passage of other substances, such as potentially interfering substances. In one embodiment, the interference domain is constructed of polyurethane. In an alternative embodiment, the interference domain comprises a high oxygen soluble polymer, such as silicone.

In some embodiments, the interference domain is formed from one or more cellulosic derivatives. In general, cellulosic derivatives may include polymers such as cellulose acetate, cellulose acetate butyrate, 2-hydroxyethyl cellulose, cellulose acetate phthalate, cellulose acetate propionate, cellulose acetate trimellitate, or blends and combinations thereof.

In some alternative embodiments, other polymer types that can be utilized as a base material for the interference domain include polyurethanes, polymers having pendant ionic groups, and polymers having controlled pore size, for example. In one such alternative embodiment, the interference domain includes a thin, hydrophobic membrane that is non-swellable and restricts diffusion of low molecular weight species. The interference domain is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Pat. No. 7,074,307, U.S. Patent Publication No. US-2005-0176136-A1, U.S. Pat. No. 7,081,195, and U.S. Patent Publication No. US-2005-0143635-A1, each of which is incorporated by reference herein in its entirety.

It is contemplated that in some embodiments, the thickness of the interference domain may be from about 0.01 microns or less to about 20 microns or more. In some of these embodiments, the thickness of the interference domain may be between about 0.01, 0.05, 0.1, 0.15, 0.2, 0.25, 0.3, 0.35, 0.4, 0.45, 0.5, 1, 1.5, 2, 2.5, 3, or 3.5 microns and about 4, 5, 6, 7, 8, 9, 10, 11, 12, 13, 14, 15, 16, 17, 18, 19, or 19.5 microns. In some of these embodiments, the thickness of the interference domain may be from about 0.2, 0.4, 0.5, or 0.6, microns to about 0.8, 0.9, 1, 1.5, 2, 3, or 4 microns.

In general, the membrane systems described herein may be formed or deposited on the exposed electroactive surfaces (e.g., one or more of the working and reference electrodes) using known thin film techniques (for example, casting, spray coating, drawing down, electro-depositing, dip coating, and the like), however casting or other known application techniques can also be utilized. In some embodiments, the interference domain may be deposited by spray or dip coating. In one exemplary embodiment, the interference domain is formed by dip coating the sensor into an interference domain solution using an insertion rate of from about 0.5 inch/min to about 60 inches/min, and sometimes about 1 inch/min; a dwell time of from about 0.01 minutes to about 2 minutes, and sometimes about 1 minute; and a withdrawal rate of from about 0.5 inch/minute to about 60 inches/minute, and sometimes about 1 inch/minute; and curing (drying) the domain from about 1 minute to about 14 hours, and sometimes from about 3 minutes to about 15 minutes (and can be accomplished at room temperature or under vacuum, e.g., 20 to 30 mmHg). In one exemplary embodiment including a cellulose acetate butyrate interference domain, a 3-minute cure (i.e., dry) time is used between each layer applied. In another exemplary embodiment employing a cellulose acetate interference domain, a 15 minute cure time is used between each layer applied.

In some embodiments, the dip process can be repeated at least one time and up to 10 times or more. In other embodiments, only one dip is preferred. The preferred number of repeated dip processes may depend upon the cellulosic derivative(s) used, their concentration, conditions during deposition (e.g., dipping) and the desired thickness (e.g., sufficient thickness to provide functional blocking of certain interferents), and the like. In one embodiment, an interference domain is formed from three layers of cellulose acetate butyrate. In another embodiment, an interference domain is formed from 10 layers of cellulose acetate. In yet another embodiment, an interference domain is formed from 1 layer of a blend of cellulose acetate and cellulose acetate butyrate. In alternative embodiments, the interference domain can be formed using any known method and combination of cellulose acetate and cellulose acetate butyrate, as will be appreciated by one skilled in the art.

Electrode Domain

It is contemplated that in some embodiments, such as the embodiment illustrated in FIG. 2C, an optional electrode domain 36, also referred to as the electrode layer, may be provided, in addition to the bioprotective domain and the enzyme domain; however, in other embodiments, the functionality of the electrode domain may be incorporated into the bioprotective domain so as to provide a unitary domain that includes the functionality of the bioprotective domain, diffusion resistance domain, enzyme domain, and electrode domain.

In some embodiments, the electrode domain is located most proximal to the electrochemically reactive surfaces. To facilitate electrochemical reaction, the electrode domain may include a semipermeable coating that maintains hydrophilicity at the electrochemically reactive surfaces of the sensor interface. The electrode domain can enhance the stability of an adjacent domain by protecting and supporting the material that makes up the adjacent domain. The electrode domain may also assist in stabilizing the operation of the device by overcoming electrode start-up problems and drifting problems caused by inadequate electrolyte. The buffered electrolyte solution contained in the electrode domain may also protect against pH-mediated damage that can result from the formation of a large pH gradient between the substantially hydrophobic interference domain and the electrodes due to the electrochemical activity of the electrodes.

In some embodiments, the electrode domain includes a flexible, water-swellable, substantially solid gel-like film (e.g. a hydrogel) having a 'dry film' thickness of from about 0.05 microns to about 100 microns, and sometimes from about 0.05, 0.1, 0.15, 0.2, 0.25, 0.3, 0.35, 0.4, 0.45, 0.5, 1 microns to about 1.5, 2, 2.5, 3, or 3.5, 4, 4.5, 5, 6, 6.5, 7, 7.5, 8, 8.5, 9, 9.5, 10, 10.5, 11, 11.5, 12, 13, 14, 15, 16, 17, 18, 19, 19.5, 20, 30, 40, 50, 60, 70, 80, 90, or 100 microns. In some embodiments, the thickness of the electrode domain may be from about 2, 2.5 or 3 microns to about 3.5, 4, 4.5, or 5 microns in the case of a transcutaneously implanted sensor, or from about 6, 7, or 8 microns to about 9, 10, 11, or 12 microns in the case of a wholly implanted sensor. The term 'dry film thickness' as used herein is a broad term, and is to be given its ordinary and customary meaning to a person of ordinary skill in the art (and is not to be limited to a special or customized meaning), and refers without limitation to the thickness of a cured film cast from a coating formulation onto the surface of the membrane by standard coating techniques. The coating formulation may comprise a premix of film-forming polymers and a crosslinking agent and may be curable upon the application of moderate heat.

In certain embodiments, the electrode domain may be formed of a curable mixture of a urethane polymer and a hydrophilic polymer. In some of these embodiments, coatings are formed of a polyurethane polymer having anionic carboxylate functional groups and non-ionic hydrophilic polyether segments, which are crosslinked in the presence of polyvinylpyrrolidone and cured at a moderate temperature of about 50° C.

Particularly suitable for this purpose are aqueous dispersions of fully-reacted colloidal polyurethane polymers having cross-linkable carboxyl functionality (e.g., BAYBOND®; Mobay Corporation). These polymers are supplied in dispersion grades having a polycarbonate-polyurethane backbone containing carboxylate groups identified as XW-121 and W-123; and a polyester-polyurethane backbone containing carboxylate groups, identified as W-110-2. In some embodiments, BAYBOND® 123, an aqueous anionic dispersion of an aliphate polycarbonate urethane polymer sold as a 35 weight percent solution in water and co-solvent N-methyl-2-pyrrolidone, may be used.

In some embodiments, the electrode domain is formed from a hydrophilic polymer that renders the electrode domain equally or more hydrophilic than an overlying domain (e.g., interference domain, enzyme domain). Such hydrophilic polymers may include, a polyamide, a polylactone, a polyimide, a polylactam, a functionalized polyamide, a functionalized polylactone, a functionalized polyimide, a functionalized polylactam or combinations thereof, for example.

In some embodiments, the electrode domain is formed primarily from a hydrophilic polymer, and in some of these embodiments, the electrode domain is formed substantially from PVP. PVP is a hydrophilic water-soluble polymer and is available commercially in a range of viscosity grades and average molecular weights ranging from about 18,000 to about 500,000, under the PVP K® homopolymer series by BASF Wyandotte and by GAF Corporation. In certain embodiments, a PVP homopolymer having an average molecular weight of about 360,000 identified as PVP-K90 (BASF Wyandotte) may be used to form the electrode domain. Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

In certain embodiments, the electrode domain is formed entirely from a hydrophilic polymer. Useful hydrophilic polymers contemplated include, but are not limited to, poly-N-vinylpyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N,N-dimethylacrylamide, polyvinyl alcohol, polyacrylic acid, polyethylene oxide, poly-2-ethyl-oxazoline, copolymers thereof and mixtures thereof. A blend of two or more hydrophilic polymers may be preferred in some embodiments.

It is contemplated that in certain embodiments, the hydrophilic polymer used may not be crosslinked, but in other embodiments, crosslinking may be used and achieved by any of a variety of methods, for example, by adding a crosslinking agent. In some embodiments, a polyurethane polymer may be crosslinked in the presence of PVP by preparing a premix of the polymers and adding a crosslinking agent just prior to the production of the membrane. Suitable cross-linking agents contemplated include, but are not limited to, carbodiimides (e.g. 1-ethyl-3-(3-dimethylaminopropyl) carbodiimide hydrochloride, and UCARLNK® XL-25 (Union Carbide)), epoxides and melamine/formaldehyde resins. Alternatively, it is also contemplated that crosslinking may be achieved by irradiation at a wavelength sufficient to promote crosslinking between the hydrophilic polymer molecules, which is believed to create a more tortuous diffusion path through the domain.

The flexibility and hardness of the coating can be varied as desired by varying the dry weight solids of the components in the coating formulation. The term 'dry weight solids' as used herein is a broad term, and is to be given its ordinary and customary meaning to a person of ordinary skill in the art (and is not to be limited to a special or customized meaning), and refers without limitation to the dry weight percent based on the total coating composition after the time the crosslinker is included. In one embodiment, a coating formulation can contain about 6 to about 20 dry weight percent, preferably about 8 dry weight percent, PVP; about 3 to about 10 dry weight percent, sometimes about 5 dry weight percent cross-linking agent; and about 70 to about 91 weight percent, sometimes about 87 weight percent of a polyurethane polymer, such as a polycarbonate-polyurethane polymer, for example. The reaction product of such a coating formulation is referred to herein as a water-swellable cross-linked matrix of polyurethane and PVP.

In some embodiments, underlying the electrode domain is an electrolyte phase that when hydrated is a free-fluid phase including a solution containing at least one compound, typically a soluble chloride salt, which conducts electric current. In one embodiment wherein the membrane system is used with a glucose sensor such as is described herein, the electrolyte phase flows over the electrodes and is in contact with the electrode domain. It is contemplated that certain embodiments may use any suitable electrolyte solution, including standard, commercially available solutions. Generally, the electrolyte phase can have the same osmotic pressure or a lower osmotic pressure than the sample being analyzed. In preferred embodiments, the electrolyte phase comprises normal saline.

Bioactive Agents

It is contemplated that any of a variety of bioactive (therapeutic) agents can be used with the analyte sensor systems described herein, such as the analyte sensor system shown in FIG. 1. In some embodiments, the bioactive agent is an anticoagulant. The term 'anticoagulant' as used herein is a broad term, and is to be given its ordinary and customary meaning to a person of ordinary skill in the art (and is not to be limited to a special or customized meaning), and refers without limitation to a substance the prevents coagulation (e.g. minimizes, reduces, or stops clotting of blood). In these embodiments, the anticoagulant included in the analyte sensor system may prevent coagulation within or on the sensor. Suitable anticoagulants for incorporation into the sensor system include, but are not limited to, vitamin K antagonists (e.g. Acenocoumarol, Clorindione, Dicumarol (Dicoumarol), Diphenadione, Ethyl biscoumacetate, Phenprocoumon, Phenindione, Tioclomarol, or Warfarin), heparin group anticoagulants (e.g. Platelet aggregation inhibitors: Antithrombin III, Bemiparin, Dalteparin, Danaparoid, Enoxaparin, Heparin, Nadroparin, Parnaparin, Reviparin, Sulodexide, Tinzaparin), other platelet aggregation inhibitors (e.g. Abciximab, Acetylsalicylic acid (Aspirin), Aloxiprin, Beraprost, Ditazole, Carbasalate calcium, Cloricromen, Clopidogrel, Dipyridamole, Epoprostenol, Eptifibatide, Indobufen, Iloprost, Picotamide, Ticlopidine, Tirofiban, Treprostinil, Triflusal), enzymes (e.g., Alteplase, Ancrod, Anistreplase, Brinase, Drotrecogin alfa, Fibrinolysin, Protein C, Reteplase, Saruplase, Streptokinase, Tenecteplase, Urokinase), direct thrombin inhibitors (e.g., Argatroban, Bivalirudin, Desirudin, Lepirudin, Melagatran, Ximelagatran, other antithrombotics (e.g., Dabigatran, Defibrotide, Dermatan sulfate, Fondaparinux, Rivaroxaban), and the like.

In one embodiment, heparin is incorporated into the analyte sensor system, for example by dipping or spraying. While not wishing to be bound by theory, it is believed that heparin coated on the catheter or sensor may prevent aggregation and clotting of blood on the analyte sensor system, thereby preventing thromboembolization (e.g., prevention of blood flow by the thrombus or clot) or subsequent complications. In some embodiments, heparin is admixed with one or more zwitterionic compounds or derivatives thereof, such as hydrolyzable cationic esters thereof (as described above), prior to dipping or spraying, thus providing the sensor system with a mixed coating of heparin and one or more zwitterionic compounds or derivatives thereof.

In some embodiments, an antimicrobial is coated on the catheter (inner or outer diameter) or sensor. In some embodiments, an antimicrobial agent may be incorporated into the analyte sensor system. The antimicrobial agents contemplated may include, but are not limited to, antibiotics, antiseptics, disinfectants and synthetic moieties, and combinations thereof, and other agents that are soluble in organic solvents such as alcohols, ketones, ethers, aldehydes, acetonitrile, acetic acid, methylene chloride and chloroform. The amount of each antimicrobial agent used to impregnate the medical device varies to some extent, but is at least of an effective concentration to inhibit the growth of bacterial and fungal organisms, such as staphylococci, gram-positive bacteria, gram-negative bacilli and *Candida*.

In some embodiments, an antibiotic may be incorporated into the analyte sensor system. Classes of antibiotics that can be used include tetracyclines (e.g., minocycline), rifamycins (e.g., rifampin), macrolides (e.g., erythromycin), penicillins (e.g., nafeillin), cephalosporins (e.g., cefazolin), other beta-lactam antibiotics (e.g., imipenem, aztreonam), aminoglycosides (e.g., gentamicin), chloramphenicol, sulfonamides (e.g., sulfamethoxazole), glycopeptides (e.g., vancomycin), quinolones (e.g., ciprofloxacin), fusidic acid, trimethoprim, metronidazole, clindamycin, mupirocin, polyenes (e.g., amphotericin B), azoles (e.g., fluconazole), and beta-lactam inhibitors (e.g., sulbactam).

Examples of specific antibiotics that can be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin.

In some embodiments, an antiseptic or disinfectant may be incorporated into the analyte sensor system. Examples of antiseptics and disinfectants are hexachlorophene, cationic bisiguanides (e.g. chlorhexidine, cyclohexidine) iodine and iodophores (e.g. povidoneiodine), para-chloro-meta-xylenol, triclosan, furan medical preparations (e.g. nitrofurantoin, nitrofurazone), methenamine, aldehydes (glutaraldehyde, formaldehyde) and alcohols. Other examples of antiseptics and disinfectants will readily suggest themselves to those of ordinary skill in the art.

In some embodiments, an anti-barrier cell agent may be incorporated into the analyte sensor system. Anti-barrier cell agents may include compounds exhibiting effects on macrophages and foreign body giant cells (FBGCs). It is believed that anti-barrier cell agents prevent closure of the barrier to solute transport presented by macrophages and FBGCs at the device-tissue interface during FBC maturation. Anti-barrier cell agents may provide anti-inflammatory or immunosuppressive mechanisms that affect the wound healing process, for example, healing of the wound created by the incision into which an implantable device is inserted. Cyclosporine, which stimulates very high levels of neovascularization around biomaterials, can be incorporated into a bioprotective membrane of a preferred embodiment (see U.S. Pat. No. 5,569,462 to Martinson et al.). Alternatively, Dexamethasone, which abates the intensity of the FBC response at the tissue-device interface, can be incorporated into a bioprotective membrane of a preferred embodiment. Alternatively, Rapamycin, which is a potent specific inhibitor of some macrophage inflammatory functions, can be incorporated into a bioprotective membrane of a preferred embodiment.

In some embodiments, an anti-inflammatory agent may be incorporated into the analyte sensor system to reduce acute or chronic inflammation adjacent to the implant or to decrease the formation of a FBC capsule to reduce or prevent barrier cell layer formation, for example. Suitable anti-inflammatory agents include but are not limited to, for example, nonsteroidal anti-inflammatory drugs (NSAIDS) such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

In some embodiments, an immunosuppressive or immunomodulatory agent may be incorporated into the analyte sensor system in order to interfere directly with several key mechanisms necessary for involvement of different cellular elements in the inflammatory response. Suitable immunosuppressive and immunomodulatory agents include, but are not limited to, anti-proliferative, cell-cycle inhibitors, (for example, paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, and advanced coatings.

In some embodiments, an anti-infective agent may be incorporated into the analyte sensor system. In general, anti-infective agents are substances capable of acting against infection by inhibiting the spread of an infectious agent or by killing the infectious agent outright, which can serve to reduce an immuno-response without an inflammatory response at the implant site, for example. Anti-infective agents include, but are not limited to, anthelmintics (e.g. mebendazole), antibiotics (e.g. aminoclycosides, gentamicin, neomycin, tobramycin), antifungal antibiotics (e.g. amphotericin b, fluconazole, griseofulvin, itraconazole, ketoconazole, nystatin, micatin, tolnaftate), cephalosporins (e.g. cefaclor, cefazolin, cefotaxime, ceftazidime, ceftriaxone, cefuroxime, cephalexin), beta-lactam antibiotics (e.g. cefotetan, meropenem), chloramphenicol, macrolides (e.g. azithromycin, clarithromycin, erythromycin), penicillins (e.g. penicillin G sodium salt, amoxicillin, ampicillin, dicloxacillin, nafcillin, piperacillin, ticarcillin), tetracyclines (e.g. doxycycline, minocycline, tetracycline), bacitracin, clindamycin, colistimethate sodium, polymyxin b sulfate, vancomycin, antivirals (e.g. acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine), quinolones (e.g. ciprofloxacin, levofloxacin); sulfonamides (e.g. sulfadiazine, sulfisoxazole), sulfones (e.g. dapsone), furazolidone, metronidazole, pentamidine, sulfanilamidum crystallinum, gatifloxacin, and sulfamethoxazole/trimethoprim.

In some embodiments, a vascularization agent may be incorporated into the analyte sensor system. Vascularization agents generally may include substances with direct or indirect angiogenic properties. In some cases, vascularization agents may additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation; however, while not wishing to be bound by theory, it is believed that some barrier-cell effects can result indirectly from the effects of vascularization agents.

Vascularization agents may provide mechanisms that promote neovascularization and accelerate wound healing around the membrane or minimize periods of ischemia by increasing vascularization close to the tissue-device interface. Sphingosine-1-Phosphate (S1P), a phospholipid possessing potent angiogenic activity, may be incorporated into the bioprotective membrane. Monobutyrin, a vasodilator and angiogenic lipid product of adipocytes, may also be incorporated into the bioprotective membrane. In another embodiment, an anti-sense molecule (for example, thrombospondin-2 anti-sense), which may increase vascularization, is incorporated into a bioprotective membrane.

Vascularization agents may provide mechanisms that promote inflammation, which is believed to cause accelerated neovascularization and wound healing in vivo. In one embodiment, a xenogenic carrier, for example, bovine collagen, which by its foreign nature invokes an immune response, stimulates neovascularization, and is incorporated into a bioprotective membrane of some embodiments. In another embodiment, Lipopolysaccharide, an immunostimulant, may be incorporated into a bioprotective membrane. In another embodiment, a protein, for example, a bone morphogenetic protein (BMP), which is known to modulate bone healing in tissue, may be incorporated into the bioprotective membrane.

In some embodiments, an angiogenic agent may be incorporated into the analyte sensor system. Angiogenic agents are substances capable of stimulating neovascularization, which can accelerate and sustain the development of a vascularized tissue bed at the tissue-device interface, for example. Angiogenic agents include, but are not limited to, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-β), Transforming Growth Factor Alpha (TGF-Alpha), Hepatocyte Growth Factor, Tumor Necrosis Factor-Alpha (TNFα), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Copper Sulphate, Estradiol, prostaglandins, cox inhibitors, endothelial cell binding agents (for example, decorin or vimentin), glenipin, hydrogen peroxide, nicotine, and Growth Hormone.

In some embodiments, a pro-inflammatory agent may be incorporated into the analyte sensor system. Pro-inflammatory agents are generally substances capable of stimulating an immune response in host tissue, which can accelerate or sustain formation of a mature vascularized tissue bed. For example, pro-inflammatory agents are generally irritants or other substances that induce chronic inflammation and chronic granular response at the wound-site. While not wishing to be bound by theory, it is believed that formation of high tissue granulation induces blood vessels, which supply an adequate or rich supply of analytes to the device-tissue interface. Pro-inflammatory agents include, but are not limited to, xenogenic carriers, Lipopolysaccharides, *S. aureus* peptidoglycan, and proteins.

These bioactive agents can be used alone or in combination. The bioactive agents can be dispersed throughout the material of the sensor, for example, incorporated into at least a portion of the membrane system, or incorporated into the device (e.g., housing) and adapted to diffuse through the membrane.

There are a variety of systems and methods by which a bioactive agent may be incorporated into the sensor membrane. In some embodiments, the bioactive agent may be incorporated at the time of manufacture of the membrane system. For example, the bioactive agent can be blended prior to curing the membrane system, or subsequent to membrane system manufacture, for example, by coating, imbibing, solvent-casting, or sorption of the bioactive agent into the membrane system. Although in some embodiments the bioactive agent is incorporated into the membrane system, in other embodiments the bioactive agent can be administered concurrently with, prior to, or after insertion of the device in vivo, for example, by oral administration, or locally, by subcutaneous injection near the implantation site. A combination of bioactive agent incorporated in the membrane system and bioactive agent administration locally or systemically can be preferred in certain embodiments.

In general, a bioactive agent can be incorporated into the membrane system, or incorporated into the device and adapted to diffuse therefrom, in order to modify the in vivo response of the host to the membrane. In some embodiments, the bioactive agent may be incorporated only into a portion of the membrane system adjacent to the sensing region of the device, over the entire surface of the device except over the sensing region, or any combination thereof, which can be helpful in controlling different mechanisms or stages of in vivo response (e.g., thrombus formation). In some alternative embodiments however, the bioactive agent may be incorporated into the device proximal to the membrane system, such that the bioactive agent diffuses through the membrane system to the host circulatory system.

The bioactive agent can include a carrier matrix, wherein the matrix includes one or more of collagen, a particulate matrix, a resorbable or non-resorbable matrix, a controlled-release matrix, or a gel. In some embodiments, the carrier matrix includes a reservoir, wherein a bioactive agent is encapsulated within a microcapsule. The carrier matrix can include a system in which a bioactive agent is physically entrapped within a polymer network. In some embodiments, the bioactive agent is cross-linked with the membrane system, while in others the bioactive agent is sorbed into the membrane system, for example, by adsorption, absorption, or imbibing. The bioactive agent can be deposited in or on the membrane system, for example, by coating, filling, or solvent casting. In certain embodiments, ionic and nonionic surfactants, detergents, micelles, emulsifiers, demulsifiers, stabilizers, aqueous and oleaginous carriers, solvents, preservatives, antioxidants, or buffering agents are used to incorporate the bioactive agent into the membrane system.

In some embodiments, the surface of the membrane system comprises a tie layer found on the outermost surface of the sensor membrane to which the bioactive agent reversibly binds. In some embodiments, this tie layer comprises one or more zwitterionic compounds, or precursors or derivatives thereof, that are bound to surface-active end groups of the polymer comprising the outermost domain of the membrane system. In some embodiments, the zwitterionic compounds or precursors or derivatives thereof comprise one or more zwitterionic betaines, as described above. In some embodiments, the zwitterionic compounds or precursors or derivatives thereof comprise hydrolyzable cationic esters of a zwitterionic compound, as described above. In preferred embodiments, the tie layer comprises one or more hydrolyzable cationic betaine esters, such as hydrolyzable cationic pCB esters.

The bioactive agent also can be incorporated into a polymer using techniques such as described above, and the polymer can be used to form the membrane system, coatings on the membrane system, portions of the membrane system, or any portion of the sensor system.

The membrane system can be manufactured using techniques known in the art. The bioactive agent can be sorbed into the membrane system, for example, by soaking the membrane system for a length of time (for example, from about an hour or less to about a week, or more preferably from about 4, 8, 12, 16, or 20 hours to about 1, 2, 3, 4, 5, or 7 days).

The bioactive agent can be blended into uncured polymer prior to forming the membrane system. The membrane system is then cured and the bioactive agent thereby cross-linked or encapsulated within the polymer that forms the membrane system.

In yet another embodiment, microspheres are used to encapsulate the bioactive agent. The microspheres can be formed of biodegradable polymers, most preferably synthetic polymers or natural polymers such as proteins and polysaccharides. As used herein, the term polymer is used to refer to both to synthetic polymers and proteins. U.S. Pat. No. 6,281,015 discloses some systems and methods that can be used in conjunction with the preferred embodiments. In general, bioactive agents can be incorporated in (1) the polymer matrix forming the microspheres, (2) microparticle(s) surrounded by the polymer which forms the microspheres, (3) a polymer core within a protein microsphere, (4) a polymer coating around a polymer microsphere, (5) mixed in with microspheres aggregated into a larger form, or (6) a combination thereof. Bioactive agents can be incorporated as particulates or by co-dissolving the factors with the polymer. Stabilizers can be incorporated by addition of the stabilizers to the factor solution prior to formation of the microspheres.

The bioactive agent can be incorporated into a hydrogel and coated or otherwise deposited in or on the membrane system. Some hydrogels suitable for use in the preferred embodiments include cross-linked, hydrophilic, three-dimensional polymer networks that are highly permeable to the bioactive agent and are triggered to release the bioactive agent based on a stimulus.

The bioactive agent can be incorporated into the membrane system by solvent casting, wherein a solution including dissolved bioactive agent is disposed on the surface of the membrane system, after which the solvent is removed to form a coating on the membrane surface.

The bioactive agent can be compounded into a plug of material, which is placed within the device, such as is described in U.S. Pat. No. 4,506,680 and U.S. Pat. No. 5,282,844. In some embodiments, it is preferred to dispose the plug beneath a membrane system; in this way, the bioactive agent is controlled by diffusion through the membrane, which provides a mechanism for sustained-release of the bioactive agent in the host.

Release of Bioactive Agents

Numerous variables can affect the pharmacokinetics of bioactive agent release. The bioactive agents of the preferred embodiments can be optimized for short- or long-term release. In some embodiments, the bioactive agents of the preferred embodiments are designed to aid or overcome factors associated with short-term effects (e.g. acute inflammation or thrombosis) of sensor insertion. In some embodiments, the bioactive agents of the preferred embodiments are designed to aid or overcome factors associated with long-term effects, for example, chronic inflammation or build-up of fibrotic tissue or plaque material. In some embodiments, the bioactive agents of the preferred embodiments combine short- and long-term release to exploit the benefits of both.

As used herein, 'controlled,' 'sustained' or 'extended' release of the factors can be continuous or discontinuous, linear or non-linear. This can be accomplished using one or more types of polymer compositions, drug loadings, selections of excipients or degradation enhancers, or other modifications, administered alone, in combination or sequentially to produce the desired effect.

Short-term release of the bioactive agent in the preferred embodiments generally refers to release over a period of from about a few minutes or hours to about 2, 3, 4, 5, 6, or 7 days or more.

Loading of Bioactive Agents

The amount of loading of the bioactive agent into the membrane system can depend upon several factors. For example, the bioactive agent dosage and duration can vary with the intended use of the membrane system, for example, the intended length of use of the device and the like; differences among patients in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above.

In some embodiments, in which the bioactive agent is incorporated into the membrane system without a carrier matrix, the preferred level of loading of the bioactive agent into the membrane system can vary depending upon the nature of the bioactive agent. The level of loading of the bioactive agent is preferably sufficiently high such that a biological effect (e.g., thrombosis prevention) is observed. Above this threshold, the bioactive agent can be loaded into the membrane system so as to imbibe up to 100% of the solid portions, cover all accessible surfaces of the membrane, or fill up to 100% of the accessible cavity space. Typically, the level of loading (based on the weight of bioactive agent(s), membrane system, and other substances present) is from about 1 ppm or less to about 1000 ppm or more, preferably from about 2, 3, 4, or 5 ppm up to about 10, 25, 50, 75, 100, 200, 300, 400, 500, 600, 700, 800, or 900 ppm. In certain embodiments, the level of loading can be 1 wt. % or less up to about 50 wt. % or more, preferably from about 2, 3, 4, 5, 6, 7, 8, 9, 10, 15, or 20 wt. % up to about 25, 30, 35, 40, or 45 wt. %.

When the bioactive agent is incorporated into the membrane system with a carrier matrix, such as a gel, the gel concentration can be optimized, for example, loaded with one or more test loadings of the bioactive agent. It is generally preferred that the gel contain from about 0.1 or less to about 50 wt. % or more of the bioactive agent(s), preferably from about 0.2, 0.3, 0.4, 0.5, 0.6, 0.7, 0.8, or 0.9 wt. % to about 6, 7, 8, 9, 10, 15, 20, 25, 30, 35, 40, or 45 wt. % or more bioactive agent(s), more preferably from about 1, 2, or 3 wt. % to about 4 or 5 wt. % of the bioactive agent(s). Substances that are not bioactive can also be incorporated into the matrix.

Referring now to microencapsulated bioactive agents, the release of the agents from these polymeric systems generally occurs by two different mechanisms. The bioactive agent can be released by diffusion through aqueous filled channels generated in the dosage form by the dissolution of the agent or by voids created by the removal of the polymer solvent or a pore forming agent during the original micro-encapsulation. Alternatively, release can be enhanced due to the degradation of the encapsulating polymer. With time, the polymer erodes and generates increased porosity and microstructure within the device. This creates additional pathways for release of the bioactive agent.

In some embodiments, the sensor is designed to be bioinert, e.g. by the use of bioinert materials. Bioinert materials do not substantially cause any response from the host. As a result, cells can live adjacent to the material but do not form a bond with it. Bioinert materials include but are not limited to alumina, zirconia, titanium oxide or other bioinert materials generally used in the 'catheter/catheterization' art. While not wishing to be bound by theory, it is believed that inclusion of a bioinert material in or on the sensor can reduce attachment of blood cells or proteins to the sensor, thrombosis or other host reactions to the sensor.

EXAMPLES

Example 1

Betaine in Outer Layer as a Surface-Active Group

Sensors are built as described in the section entitled 'Exemplary Glucose Sensor Configuration,' and include a unitary bioprotective/diffusion resistance domain comprising 2% poly(carboxyl) betaine (pCB). The presence of pCB in the outermost domain of the sensor facilitates surface wetting and speeds polymer rearrangement due to hydration. Faster polymer rearrangement improves sensor performance by reducing sensor drift.

Example 2

Polyampholytic Outer Layer (Net Neutral Charge)

Sensors are built as described in the section entitled 'Exemplary Glucose Sensor Configuration,' and include a unitary bioprotective/diffusion resistance domain. The unitary bioprotective/diffusion resistance domain is prepared from a blend of polymers comprising about 2% wt. of a co-polymer comprising about equal amounts of positively charged [2-(acryloyloxy) ethyl] trimethyl ammonium chloride (TMA) and negatively charged 2-carboxy ethyl acrylate (CAA) monomers.

Preparation of the unitary bioprotective/diffusion resistance domain from a blend comprising the positively and negatively charged monomers allows for preparation of a net neutral device surface with a relatively homogenous distribution of positive and negative charges. These charges facilitate surface wetting and speed polymer rearrangement due to hydration. The resulting devices exhibit improved sensor performance due to reduced drift.

Example 3

Surface Active End Groups that are Cross Linked to Zwitterions

Sensors are built as described in the section entitled 'Exemplary Glucose Sensor Configuration,' and include a unitary bioprotective/diffusion resistance domain comprising surface-modified end groups that are linkable to pCB.

These sensors are then dipped in a solution of carboxybetaine monomers and isocyanate, a cross-linking agent, to apply as a surface coating on the sensor. The dipped sensors are then dried under conditions suitable to trigger cross-linking of the carboxybetaine monomers and the surface-active end groups. The resulting surface coating facilitates surface wetting and speeds polymer rearrangement in the unitary bioprotective/diffusion resistance domain due to faster hydration. Faster polymer rearrangement improves sensor performance by reducing sensor drift.

Example 4

Surface Active End Groups that are Cross Linked to Zwitterions, which are then Used as a Tie Layer Sensors are built as described in the section entitled 'Exemplary Glucose Sensor Configuration,' and include a unitary bioprotective/diffusion resistance domain comprising surface-modified end groups that are cross-linkable to pCB.

These sensors are then dipped in a solution of carboxylbetaine monomers and isocyanate, a cross-linking agent, to apply as a surface coating on the sensor. The dipped sensors are then dried under conditions suitable to trigger cross-linking of the surface coating.

Once dry, the coated sensor is then soaked in a solution containing an anti-coagulant for 4-6 hours under conditions whereby the anti-coagulant is reversibly bound to the zwitterionic tie layer.

Example 5

Hydrolyzable Betaine Esters

Sensors are built as described in the section entitled 'Exemplary Glucose Sensor Configuration,' and include a unitary bioprotective/diffusion resistance domain comprising surface-modified end groups comprising about 1-2% wt. hydrolyzable cationic pCB esters.

Hydrolyzable cationic pCB esters impart several benefits to the sensor. First, hydrolysis of the cationic pCB esters leads to the release of killed microbes or the unpacking of DNA. Second, hydrolysis of the cationic pCB esters results in generation of zwitterionic betaine groups which further resist fouling by non-specific protein adsorption.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004;and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; and U.S. Patent Publication No. 2005-0182451-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; and U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS".

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A device for measurement of a glucose concentration, the device comprising:
    a sensor configured to generate a signal indicative of a glucose concentration; and
    a sensing membrane located over the sensor, wherein the sensing membrane comprises an outermost domain, wherein the outermost domain comprises a copolymer, wherein the copolymer comprises at least one betaine compound or a derivative thereof, wherein the copolymer comprises both hydrophilic and hydrophobic regions, wherein an amount of the at least one betaine compound or the derivative thereof in the outermost domain is from about 1% wt. to about 50% wt. of the outermost domain.

2. The device of claim 1, wherein the at least one betaine compound or the derivative thereof comprise at least one compound selected from the group consisting of a carboxyl betaine compound, a sulfo betaine compound, a phosphor betaine compound, and derivatives thereof.

3. The device of claim 1, wherein the at least one betaine compound or the derivative thereof comprises at least one compound selected from the group consisting of cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine), poly(sulfobetaine), and derivatives thereof.

4. The device of claim 1, wherein the at least one betaine compound or the derivative thereof comprises at least one compound selected from the group consisting of poly(carboxybetaine), poly(sulfobetaine), and derivatives thereof.

5. The device of claim 1, wherein the sensing membrane further comprises an enzyme domain comprising an enzyme selected from the group consisting of glucose oxidase, glucose dehydrogenase, galactose oxidase, cholesterol oxidase, amino acid oxidase, alcohol oxidase, lactate oxidase, and uricase.

6. The device of claim 5, wherein the enzyme is glucose oxidase.

7. The device of claim 1, wherein the membrane has a thickness from about 0.1 microns to about 1 micron.

8. The device of claim 1, wherein the membrane has a thickness from about 0.1 microns to about 0.5 micron.

9. The device of claim 1, wherein the copolymer is a polyurethane copolymer.

10. The device of claim 9, wherein the polyurethane copolymer is a polyurethane urea copolymer.

11. The device of claim 1, wherein the sensor comprises an electrode.

12. The device of claim 1, wherein the device is configured for continuous measurement of glucose concentration.

13. A device for measurement of a glucose concentration, the device comprising:
    a sensor configured to generate a signal indicative of a glucose concentration; and
    a sensing membrane located over the sensor, wherein the sensing membrane comprises an outermost domain, wherein the outermost domain comprises a copolymer, wherein the copolymer comprises at least one betaine compound or a derivative thereof, wherein the copolymer comprises both hydrophilic and hydrophobic regions, wherein an amount of the at least one betaine compound or the derivative thereof in the outermost domain is from about 10% wt. to about 40% wt. of the outermost domain.

14. The device of claim 13, wherein the at least one betaine compound or the derivative thereof comprise at least one compound selected from the group consisting of a carboxyl betaine compound, a sulfo betaine compound, a phosphor betaine compound, and derivatives thereof.

15. The device of claim 13, wherein the at least one betaine compound or the derivative thereof comprises at least one compound selected from the group consisting of cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine), poly(sulfobetaine), and derivatives thereof.

16. The device of claim 13, wherein the at least one betaine compound or the derivative thereof comprises at least one compound selected from the group consisting of poly(carboxybetaine), poly(sulfobetaine), and derivatives thereof.

17. The device of claim 13, wherein the sensing membrane further comprises an enzyme domain comprising an enzyme selected from the group consisting of glucose oxidase, glucose dehydrogenase, galactose oxidase, cholesterol oxidase, amino acid oxidase, alcohol oxidase, lactate oxidase, and uricase.

18. The device of claim 17, wherein the enzyme is glucose oxidase.

19. The device of claim 13, wherein the membrane has a thickness from about 0.1 microns to about 1 micron.

20. The device of claim 13, wherein the membrane has a thickness from about 0.1 microns to about 0.5 micron.

21. The device of claim 13, wherein the copolymer is a polyurethane copolymer.

22. The device of claim 21, wherein the polyurethane copolymer is a polyurethane urea copolymer.

23. The device of claim 13, wherein the sensor comprises an electrode.

24. The device of claim 13, wherein the device is configured for continuous measurement of glucose concentration.

* * * * *

UNITED STATES PATENT AND TRADEMARK OFFICE
CERTIFICATE OF CORRECTION

PATENT NO. : 10,045,723 B2
APPLICATION NO. : 14/543644
DATED : August 14, 2018
INVENTOR(S) : Robert J. Boock It is certified that error appears in the above-identified patent and that said Letters Patent is hereby corrected as shown below:

Column 2 (page 2, item (56)) at Line 20, Under Other Publications, change "bloelectronics." to --bioelectronics.--.

In Column 5 at Line 42, Change "andrenostenedione;" to --androstenedione;--.

In Column 5 at Line 44, Change "biotimidase;" to --biotinidase;--.

In Column 5 at Line 58, Change "diptheria/" to --diphtheria/--.

In Column 5 at Line 65, Change "perioxidase;" to --peroxidase;--.

In Column 6 at Line 4, Change "phenyloin;" to --phenytoin;--.

In Column 6 at Line 7, Change "sissomicin;" to --sisomicin;--.

In Column 6 at Line 11, Change "duodenalisa," to --duodenalis,--.

In Column 6 at Line 19, Change "Trepenoma pallidium," to --Treponema pallidum,--.

In Column 6 at Line 20, Change "stomatis" to --stomatitis--.

In Column 6 at Line 41, Change "(barbituates," to --(barbiturates,--.

In Column 6 at Line 64, Change "and or" to --and/or--.

In Column 10 at Line 51, Change "5,964,745,and" to --5,964,745, and--.

In Column 12 at Line 65, Change "Bellafonte," to --Bellefonte,--.

Signed and Sealed this
Sixth Day of November, 2018

Andrei Iancu
*Director of the United States Patent and Trademark Office*

CERTIFICATE OF CORRECTION (continued)
U.S. Pat. No. 10,045,723 B2

In Column 23 at Line 52, Change "smoothes" to --smooths--.

In Column 23 at Line 65, Change "smoothes" to --smooths--.

In Column 27 at Line 33, Change "gluteraldehyde" to --glutaraldehyde--.

In Column 41 at Line 10, Change "W-123;" to --XW-123;--.

In Column 41 at Line 11, Change "W-110-2." to --XW-110-2.--.

In Column 43 at Line 35, Change "nafeillin)," to --nafcillin),--.

In Column 43 at Line 56, Change "bisiguanides" to --biguanides--.

In Column 44 at Line 25, Change "acetometaphen," to --acetaminophen,--.

In Column 44 at Line 31, Change "melenamic" to --mefenamic--.

In Column 44 at Line 35, Change "betamethesone," to --betamethasone,--.

In Column 44 at Line 50, Change "infiximab)," to --infliximab),--.

In Column 44 at Line 53, Change "methothrexate," to --methotrexate,--.

In Column 44 at Line 54, Change "vincristing," to --vincristine,--.

In Column 44 at Line 56, Change "batimstat," to --batimastat,--.

In Column 44 at Line 59, Change "catchins," to --catechins,--.

In Column 44 at Line 61, Change "Tesosentan," to --Tezosentan,--.

In Column 44 at Line 61, Change "Cerivasttin)," to --Cerivastatin),--.

In Column 45 at Line 4, Change "aminoclycosides," to --aminoglycosides,--.

In Column 46 at Line 13, Change "Angiotropin," to --Angiotrofin,--.

In Column 46 at Line 17, Change "glenipin," to --genipin,--.

In Column 51 at Line 40, Change "8,386,004;and" to --8,386,004; and--.